(12) United States Patent
Sewell

(10) Patent No.: US 7,548,301 B2
(45) Date of Patent: *Jun. 16, 2009

(54) MASKLESS OPTICAL WRITER

(75) Inventor: Harry Sewell, Ridgefield, CT (US)

(73) Assignee: ASML Holding N.V., Veldhoven (NL)

( * ) Notice: Subject to any disclaimer, the term of this patent is extended or adjusted under 35 U.S.C. 154(b) by 300 days.

This patent is subject to a terminal disclaimer.

(21) Appl. No.: 11/337,691

(22) Filed: Jan. 24, 2006

(65) Prior Publication Data

US 2006/0119827 A1 Jun. 8, 2006

Related U.S. Application Data

(63) Continuation of application No. 10/755,470, filed on Jan. 13, 2004, now Pat. No. 7,012,674.

(51) Int. Cl.
*G03B 27/54* (2006.01)
*G03B 27/42* (2006.01)

(52) U.S. Cl. .......................... 355/67; 355/53

(58) Field of Classification Search ............ 355/53, 355/67–71; 430/5, 20, 30; 359/290, 245
See application file for complete search history.

(56) References Cited

U.S. PATENT DOCUMENTS

| | | | |
|---|---|---|---|
| 5,229,872 A | 7/1993 | Mumola | |
| 5,296,891 A | 3/1994 | Vogt et al. | |
| 5,500,736 A | 3/1996 | Koitabashi et al. | |
| 5,523,193 A | 6/1996 | Nelson | |
| 5,530,482 A | 6/1996 | Gove et al. | |
| 5,579,147 A | 11/1996 | Mori et al. | |
| 5,677,703 A | 10/1997 | Bhuva et al. | |
| 5,721,622 A | 2/1998 | Venkateswar | |

(Continued)

FOREIGN PATENT DOCUMENTS

EP    0 552 953 A1    7/1993

(Continued)

OTHER PUBLICATIONS

Search Report for European Patent Application No. 05 00 0082.7, mailed by the European Patent Office on Dec. 10, 2007, 3 pages.

(Continued)

*Primary Examiner*—Hung Henry Nguyen
(74) *Attorney, Agent, or Firm*—Sterne, Kessler, Goldstein & Fox P.L.L.C.

(57) ABSTRACT

A maskless pattern generating system for use in lithographic processing includes a liquid crystal pixel array. The system generates a light beam and applies a voltage level to each pixel of the pixel array to modulate a polarization state of the light beam so as to create a pattern image. The voltage levels correspond to greyscale levels assigned to the pixels. The system can receive a control signal input based on pattern information that defines the pattern image. The setting of the individual voltage levels can allow the liquid crystal pixel array to act as a phase shift mask, can allow the pattern image to be shifted, and can allow the manipulation of a pattern image edge. This maskless pattern writing system acts as a light valve to control pattern imagery, on a pixel by pixel basis, for the purposes of direct writing patterns.

24 Claims, 21 Drawing Sheets

U.S. PATENT DOCUMENTS

| | | | |
|---|---|---|---|
| 5,742,362 A | 4/1998 | Chikamichi | |
| 5,808,797 A | 9/1998 | Bloom et al. | |
| 5,982,553 A | 11/1999 | Bloom et al. | |
| 5,998,069 A | 12/1999 | Cutter et al. | |
| 6,084,656 A | 7/2000 | Choi et al. | |
| 6,133,986 A | 10/2000 | Johnson | |
| 6,177,980 B1 | 1/2001 | Johnson | |
| 6,291,110 B1 | 9/2001 | Cooper et al. | |
| 6,333,780 B1 | 12/2001 | Tsukuda | |
| 6,356,340 B1 | 3/2002 | Spence | |
| 6,407,766 B1 * | 6/2002 | Ramanujan et al. | 347/239 |
| 6,480,261 B2 | 11/2002 | Cooper et al. | |
| 6,504,644 B1 | 1/2003 | Sandstrom | |
| 6,544,698 B1 | 4/2003 | Fries | |
| 6,580,490 B1 | 6/2003 | Wong et al. | |
| 6,687,041 B1 | 2/2004 | Sandstrom | |
| 6,747,783 B1 | 6/2004 | Sandstrom | |
| 6,795,169 B2 | 9/2004 | Tanaka et al. | |
| 6,806,897 B2 | 10/2004 | Kataoka et al. | |
| 6,811,953 B2 | 11/2004 | Hatada et al. | |
| 6,812,477 B2 * | 11/2004 | Matsunami | 250/548 |
| 6,831,768 B1 | 12/2004 | Cebuhar et al. | |
| 6,985,280 B2 | 1/2006 | Cebuhar et al. | |
| 7,012,674 B2 * | 3/2006 | Sewell | 355/67 |
| 7,023,528 B2 * | 4/2006 | Hsu et al. | 355/71 |
| 7,095,484 B1 | 8/2006 | Fries | |
| 2002/0027647 A1 | 3/2002 | Cooper et al. | |
| 2003/0038931 A1 | 2/2003 | Toyoda et al. | |
| 2003/0122091 A1 | 7/2003 | Almogy | |
| 2004/0041104 A1 | 3/2004 | Liebregts et al. | |
| 2004/0130561 A1 | 7/2004 | Jain | |
| 2004/0145712 A1 | 7/2004 | Bleeker | |
| 2005/0007572 A1 | 1/2005 | George et al. | |
| 2005/0012916 A1 | 1/2005 | Van Der Mast et al. | |

FOREIGN PATENT DOCUMENTS

| | | |
|---|---|---|
| EP | 1 503 245 A2 | 2/2005 |
| JP | 8-97119 A | 4/1996 |
| JP | 2002-506236 A | 2/2002 |
| WO | WO 98/33096 | 7/1998 |
| WO | WO 98/38597 | 9/1998 |
| WO | WO 99/45441 A1 | 9/1999 |
| WO | WO 2004/001508 A2 | 12/2003 |
| WO | WO 2004/001508 A3 | 12/2003 |

OTHER PUBLICATIONS

English abstract of Taiwan Patent Publication No. 554411 B, published Sep. 21, 2003, 1 page.

Search Report and translation of Search Report for Taiwan Patent Application No. 094100282, completed by the Intellectual Property Office (IPO) on Nov. 6, 2007, 2 pages.

Translation of Office Action for Japanese Patent Application No. 2005-006630 mailed Feb. 26, 2008, 3 pgs.

Office Action for Chinese Application No. 200510004345.5 issued May 30, 2008, 8 pgs.

Janssen, P., et al., "Design aspects of a scrolling color LCoS display," Displays, vol. 23, Issue 3, pp. 99-108, Elsevier Science B.V., Jun. 2002.

"Large-Screen, High-Resolution Projection Displays," Philips Research Password, Issue 4, pp. 16-19, Jul. 2000.

Search Report for Singapore Patent Application No. 200500026-0, mailed by the Australian Patent Office on Aug. 17, 2005, 3 pages.

Translation of Office Action for Japanese Patent Application No. 2005-006630 mailed Feb. 26, 2008, 3 pgs.

* cited by examiner

MASKLESS OPTICAL WRITER

CROSS-REFERENCE TO RELATED APPLICATIONS

This application is a continuation of U.S. patent application Ser. No. 10/755,470, filed Jan. 13, 2004 which is now U.S. Pat. 7,012,674 the contents of which is hereby incorporated by reference in its entirety.

BACKGROUND OF THE INVENTION

1. Field of the Invention

This invention relates generally to lithographic processing. More particularly, this invention relates to a maskless optical writer for direct writing high resolution patterns to substrates such as integrated circuit wafers.

2. Background Art

Lithography is a process used to create features on the surface of substrates. Such substrates can include those used in the manufacture of flat panel displays, circuit boards, various integrated circuits, and the like. A frequently used substrate for such applications is a semiconductor wafer. During lithography, a wafer is disposed on a wafer stage and held in place by a chuck. The chuck is typically a vacuum or electrostatic chuck capable of securely holding the wafer in place. The wafer is exposed to an image projected onto its surface by exposure optics located within a lithography apparatus. While exposure optics are used in the case of photolithography, a different type of exposure apparatus can be used depending on the particular application. For example, x-ray, ion, electron, or photon lithographies each may require a different exposure apparatus, as is known to those skilled in the relevant art. The particular example of photolithography is discussed here for illustrative purposes only.

The projected image produces changes in the characteristics of a layer, for example photoresist, deposited on the surface of the wafer. These changes correspond to the features projected onto the wafer during exposure. Subsequent to exposure, the layer can be etched to produce a patterned layer. The pattern corresponds to those features projected onto the wafer during exposure. This patterned layer is then used to remove, dope, or otherwise affect exposed portions of underlying structural layers within the wafer, such as conductive, semiconductive, or insulative layers. This process is then repeated, together with other steps, until the desired features have been formed on the surface, or in various layers, of the wafer.

Step-and-scan technology works in conjunction with a projection optics system that has a narrow imaging slot. Rather than expose the entire wafer at one time, individual fields are scanned onto the wafer one at a time. This is done by moving the wafer and the reticle or light valve that defines the pattern simultaneously such that the imaging slot is moved across the field during the scan. The wafer stage must then be stepped between field exposures to allow multiple copies of a pattern to be exposed over the wafer surface. In this manner, the sharpness of the image projected onto the wafer is maximized.

Reticles (also known as masks or photomasks) are used to block photoresist exposure in selected areas, defining the pattern to be exposed. Reticles, and the use of reticles, can be expensive, especially for small wafer runs.

An alternative to using reticles is to use a maskless light valve called a spatial light modulator (SLM), such as a grating light valve (GLV) or a digital micromirror device (DMD) (also known as a digital micromirror array or a tilt-mirror array). A DMD is an array of a multitude of tiny mirrors, each mirror representing one pixel of a pattern. Each micromirror can be individually programmed to be turned on or off, thereby allowing the micromirror array to be programmed to represent a desired pattern. When an individual micromirror is turned on, an illumination is reflected by that mirror toward exposure optics and ultimately to a photoresist or substrate (e.g., a wafer). When an individual micromirror is turned off, the illumination is not reflected toward the exposure optics and therefore is not then reflected toward the photoresist or substrate. In this way, the DMD becomes a maskless light valve.

One disadvantage of using a DMD is that micromirrors generally can only be on or off. In other words, a DMD does not easily allow greyscaling. In order to change greyscaling using a DMD, the micromirror needs to be precisely tilted to an exact angle. However, the customized tilting of the micromirror can have negative effects. For example, telecentricity may change due the image plane no longer being orthogonal to the optics as a result of a mirror tilt. In addition, with a DMD, one does not have control of the phase of the light for individual pixels. Therefore, a DMD cannot easily be used as a phase shift mask.

What is needed is a maskless optical writer for direct writing patterns to substrates, without the disadvantages associated with reticle systems and known light valve systems described above.

BRIEF SUMMARY OF THE INVENTION

A maskless pattern generating system for use in lithographic processing includes a liquid crystal pixel array. The system generates a light beam and applies a voltage level to each pixel of the pixel array to modulate a polarization state of the light beam so as to create a pattern image. The voltage levels correspond to greyscale levels assigned to the pixels. The system can receive a control signal input based on pattern information that defines the pattern image. This maskless pattern writing system acts as a light valve to control pattern imagery, on a pixel by pixel basis, for the purposes of direct writing patterns.

One advantage of the invention is that the programmable pattern generator can be used as a phase shift mask. The pattern image can become phase-shifted when the individual voltage levels applied to the pixels of the pixel array are set past one cycle of light. Another advantage is that placement of the pattern image can be shifted when the individual voltage levels set for the pixels corresponding to the pattern image are shifted in one direction by the same number of pixel rows. A further advantage of this invention is that an edge of the pattern image can be manipulated by setting the individual voltage levels corresponding to the pixels that are either part of the pattern image edge or a pixel row beyond the pixels of the pattern image edge, for example.

Further embodiments, features, and advantages of the present invention, as well as the structure and operation of the various embodiments of the present invention, are described in detail below with reference to the accompanying drawings. The above features and advantages are not each required for all disclosed embodiments of the present invention.

BRIEF DESCRIPTION OF THE FIGURES

The accompanying drawings, which are incorporated herein and form part of the specification, illustrate the present invention and, together with the description, further serve to explain the principles of the invention and to enable a person skilled in the pertinent art to make and use the invention.

Figure 1:
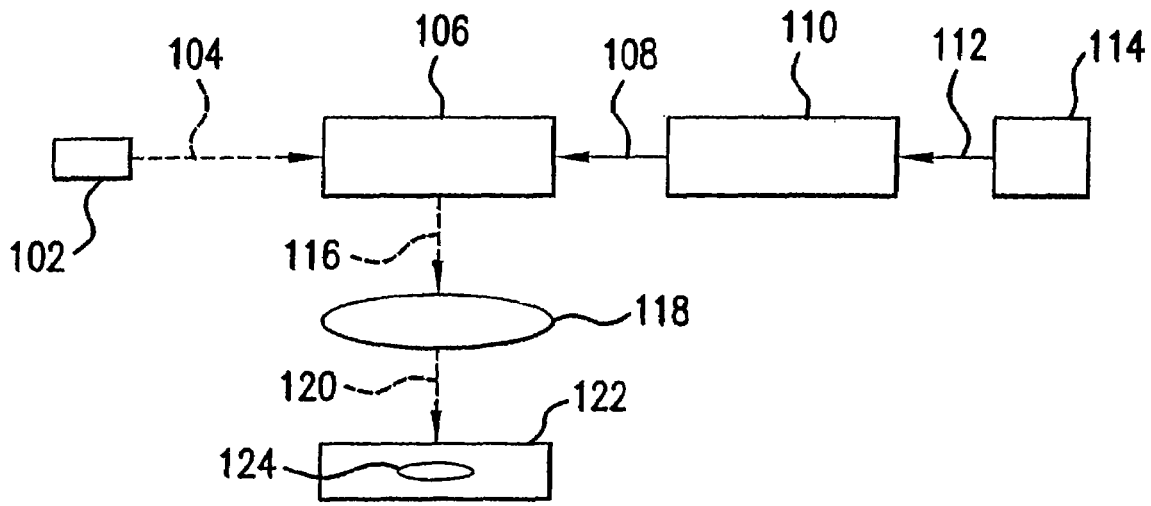
FIG. 1 is an exemplary illustration of a maskless optical writing system as is currently known by those skilled in the art.

The features and advantages of the present invention will become more apparent from the detailed description set forth below when taken in conjunction with the drawings in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

While the present invention is described herein with reference to illustrative embodiments for particular applications, it should be understood that the invention is not limited thereto. Those skilled in the art with access to the teachings provided herein will recognize additional modifications, applications, and embodiments within the scope thereof and additional fields in which the present invention would be of significant utility.

It should be noted that the terms "light," "light beam," and "illumination" are used interchangeably throughout this specification.

A conventional maskless optical writing system 100 is depicted in FIG. 1.

An illumination source 102 directs an illumination beam 104 toward a conventional pattern generator 106. The pattern generator 106 may be a DMD form of an SLM, or some type of tilt-mirror device, for example. Pattern instructions are provided to the pattern generator 106 via a control signal 108 by a controller 110. Controller 110 receives pattern information via a data stream 112 from a pattern information source 114.

In the conventional maskless optical writing system 100, pattern generator 106 turns pixels (e.g., micromirrors of a DMD) on or off according to instructions received via control signal 108. When illumination beam 104 is reflected by the "on" pixels within pattern generator 106, a generated light beam 116 results. Generated light beam 116 is reflected toward a reduction optics 118. Reduction optics 118 comprises a plurality of lenses that minimize light beam 116, thereby minimizing the pattern image. The minimized pattern image is then projected as light beam 120 onto a substrate 124 (e.g., a semiconductor wafer, flat panel display, or the like workpiece) disposed on a substrate stage 122. Substrate stage 122 may be a stepping and scanning stage, for example.

The conventional maskless pattern generator, such as a DMD, does not easily allow greyscaling. In order to change greyscaling using a DMD, each micromirror must be tilted to an exact angle. However, the customized tilting of the micromirror can have negative effects. For example, telecentricity may change due to the image plane no longer being orthogonal to the optics as a result of a mirror tilt. In addition, with a DMD, one does not have control of the phase of the light for individual pixels. Therefore, a DMD cannot easily be used as a phase shift mask.

Figure 2:
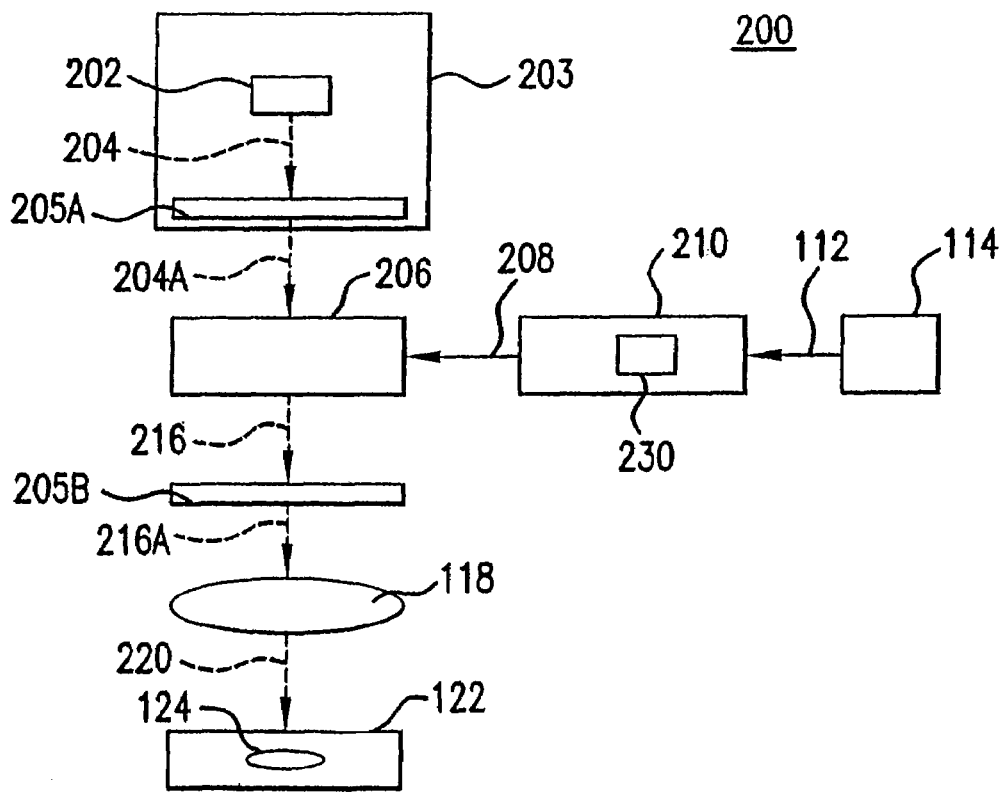
FIG. 2 is an exemplary illustration of a maskless optical writing system, according to an embodiment of the present invention.

A maskless optical writing system 200, according to an embodiment of the present invention, is depicted in FIG. 2. A polarized illumination source 203 outputs a polarized beam 204A. Polarized illumination source 203 is depicted as illumination source 202, which provides an illumination beam 204 to a polarizer 205A. Polarizer 205A polarizes illumination beam 204, resulting in a polarized illumination beam 204A. It is to be appreciated by those skilled in the art that other types of polarized illumination sources can be used. Polarized illumination beam 204A is then directed toward a non-conventional pattern generator 206.

In one embodiment of the present invention, the pattern generator 206 comprises a liquid crystal display (LCD) array. A pattern information source 114 provides a data stream 112 containing pattern information to a controller 210. Controller 210 outputs a control signal 208 that contains pattern instructions for pattern generator 206. Controller 210 can comprise hardware, software, or a combination of hardware and software.

Controller 210 comprises a pattern information manipulator 230. Pattern information manipulator 230 decodes pattern information received from data stream 112, and assigns the pattern information data on a pixel-by-pixel basis. According to an embodiment of the present invention, the pattern information manipulator 230 assigns greyscale values for each pixel. Embodiments of pattern information manipulator 230 can comprise hardware, software, or a combination of hardware and software. Pattern information manipulator 230 will be described in more detail below.

In maskless optical writing system 200, the LCD array of pattern generator 206 comprises a plurality of LCD chips. Each pixel of each LCD chip is provided with a voltage corresponding to the instructions supplied by control signal 208. The intensity of the resulting exposure on substrate 124 depends indirectly on the voltage supplied to each pixel and the resulting polarization modulation of the output light beams. It is this polarization modulation that creates the light valve, as described below.

Figure 4A:
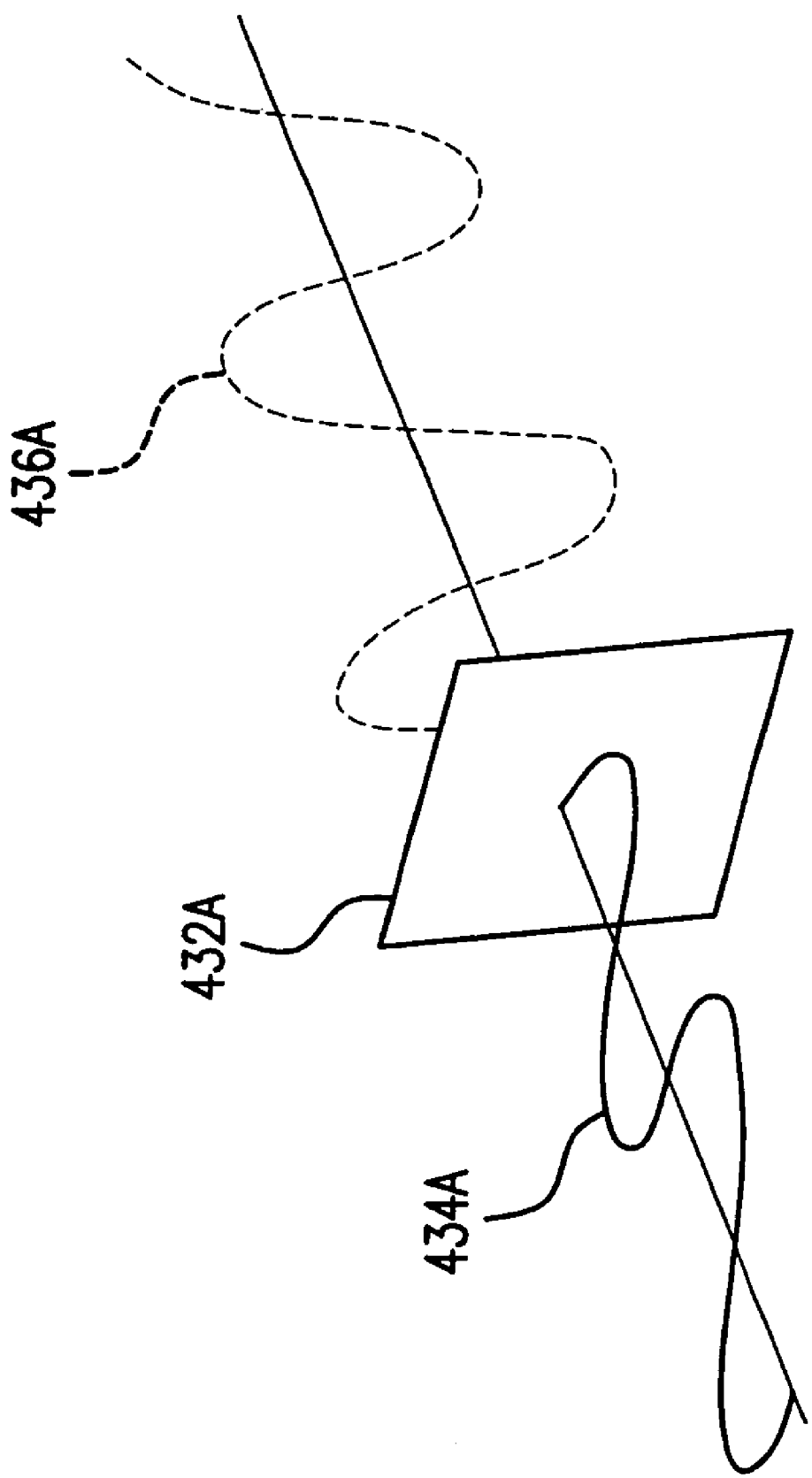
FIG. 4A illustrates the workings of a liquid crystal display, according to an embodiment of the present invention.

The general operation of an LCD array will now be discussed. As stated previously, in one embodiment of the present invention, pattern generator 206 is an LCD array, which comprises a plurality of LCD chips. Each LCD chip operates as is depicted in FIG. 4A. The type of liquid crystal (LC) employed and how that LC material behaves in the presence of an electric field will determine its polarization and whether incident light is transmitted or not (in the case of a transmissive array), as is conventionally known in the LCD art. For example, the LC material in an LCD chip may have properties such that if no voltage is applied to LCD chip 432A, the polarity of an incident polarized light beam wave 434A changes (i.e., "rotates") ninety degrees (90°). Thus, transmitted polarized light beam wave 436A is ninety degrees out of phase with respect to incident polarized light beam wave 434A. This occurs because of the refractive properties of the LC material of LCD chip 432A. Alternatively, application of a voltage to LCD chip 432A may not cause the polarity of polarized light beam wave 434A to rotate ninety degrees, thereby allowing light beam wave 434A to simply pass through with the same polarity. At voltages in-between, however, the polarization of the light is partly rotated and elliptically polarized. Alternatively, the LC material may have opposite properties such that if no voltage is applied, the polarity does not change, and if a voltage is applied, the polarity changes ninety degrees.

In one embodiment of the present invention, the liquid crystal material of the LCD array has properties such that when no voltage is supplied to a pixel, the polarity of the resulting light beam 216 from that pixel is rotated by ninety degrees. In this embodiment, when a certain voltage (a "no-polarity-change" voltage) is supplied to a pixel, the polarity of the resulting light beam 216 from that pixel does not change. If the desired result is for the pixels with no voltage supplied thereto to produce no light at all, then the light resulting from pixels with no voltage supplied thereto needs to be blocked. For this embodiment, a polarizer 205B with the same polarity as the polarity of polarized illumination beam 204A is employed. In this configuration, light beams 216 incident on pixels of LCD array 206 with no voltage supplied thereto will be at the opposite polarity as polarizer 205B and will be blocked, producing no exposure in the corresponding areas of substrate 124.

Alternatively, light beams 216 incident on pixels of LCD array 206 with the "no-polarity-change" voltage supplied will be at the same polarity as polarizer 205B and will be transmitted through as light beams 216A. Light beams 216A will then pass through reduction optics 118 as minimized light beams 220, and will expose substrate 124 at the highest intensity. At voltages supplied to the pixels that are between zero and the "no-polarity-change" voltage, the polarization of the light is partly rotated and elliptically polarized, allowing some light to pass through polarizer 205B, and therefore allowing greyscale levels to occur in light beams 216A.

In another embodiment of the present invention, the liquid crystal material of the LCD array has properties such that when a certain voltage is supplied to a pixel (e.g., a "90-degree-polarity-change" voltage), the polarity of the resulting light beam 216 from that pixel is rotated by ninety degrees. In this embodiment, when no voltage is supplied to a pixel, the polarity of the resulting light beam 216 from that pixel does not change. If the desired result is for the pixels with no voltage supplied thereto to produce no light at all, then the light resulting from pixels with no voltage supplied needs to be blocked. For this embodiment, a polarizer with a polarity opposite of the polarity of polarized illumination beam 204A is employed. In this configuration, light beams 216 incident on pixels of LCD array 206 with no voltage supplied thereto will be at the opposite polarity as polarizer 205B and will be blocked, producing no exposure in the corresponding areas of substrate 124.

Alternatively, light beams 216 incident on pixels of LCD array 206 with the "90-degree-polarity-change" voltage supplied will be at the same polarity as polarizer 205B and will be transmitted through as light beams 216A. Light beams 216A will then pass through reduction optics 118 as minimized light beams 220, and will expose substrate 124 at the highest intensity. At voltages supplied to the pixels that are between zero and the "90-degree-polarity-change" voltage, the polarization of the light is partly rotated and elliptically polarized, allowing some light to pass through polarizer 205B, and therefore allowing greyscale levels to occur in light beams 216A.

In maskless optical writing system 200, light beam 216A is minimized by reduction optics 118. Reduction optics 118 comprises a plurality of lenses.

Reduction optics 118 can encompass any suitable reduction optics for this purpose, as is to be appreciated by those skilled in the art. Minimized light beam 220 is then projected onto substrate 124 held by substrate stage 122. The intensity of the exposure on substrate 124 depends indirectly on the amount of voltage applied to each corresponding pixel of pattern generator 206, as previously described.

Figure 3:
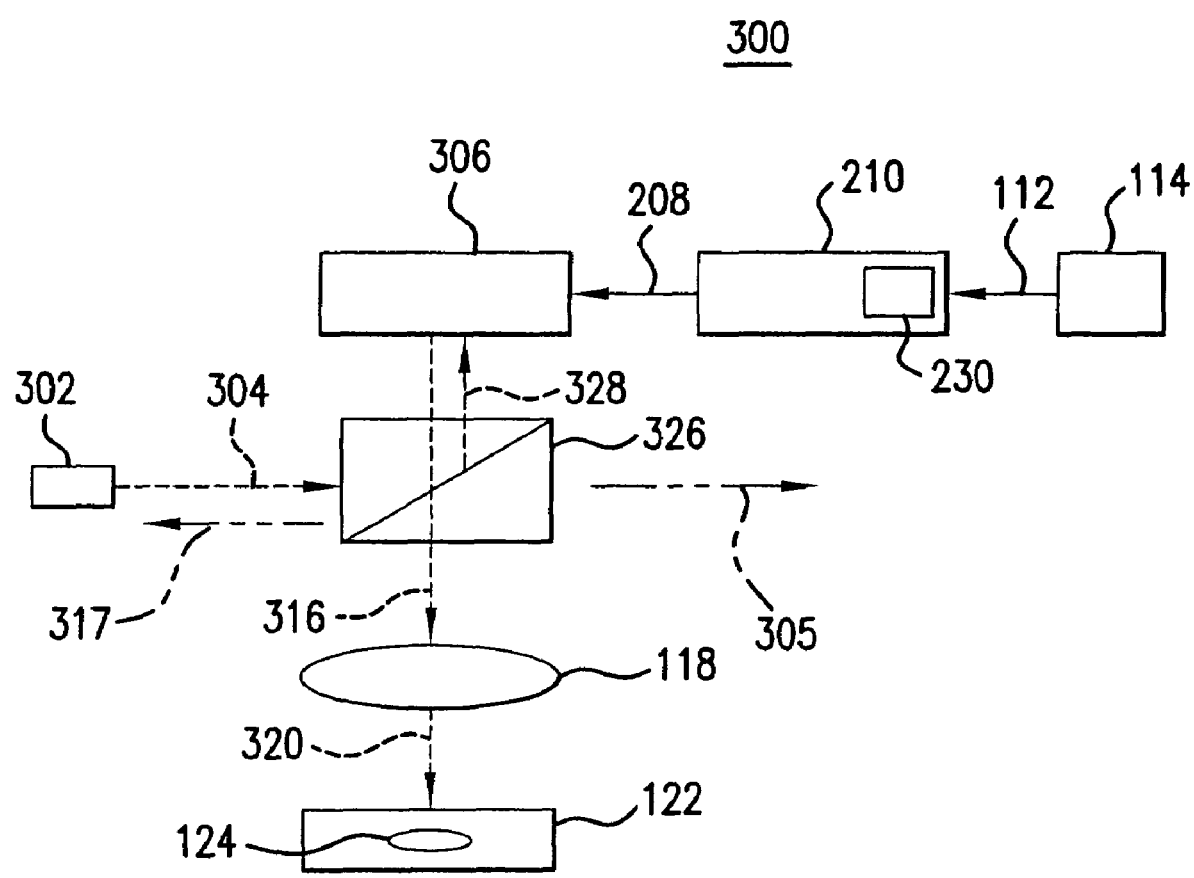
FIG. 3 is an exemplary illustration of a maskless optical writing system using polarized illumination, according to an embodiment of the present invention.

Another embodiment of the present invention is shown in FIG. 3. In maskless optical writing system 300 of FIG. 3, the function of polarizers 205A/B of FIG. 2 is performed by a single polarizing beam splitter 326. In this embodiment, pattern generator 306 is a reflective LCD (RLCD) array. A significant difference between an LCD array and an RLCD array is that the incident light beam(s) for imaging the substrate is reflected off the RLCD, rather than being transmitted through. The polarization modulation occurs similarly in both LCD and RLCD arrays.

Figure 4B:
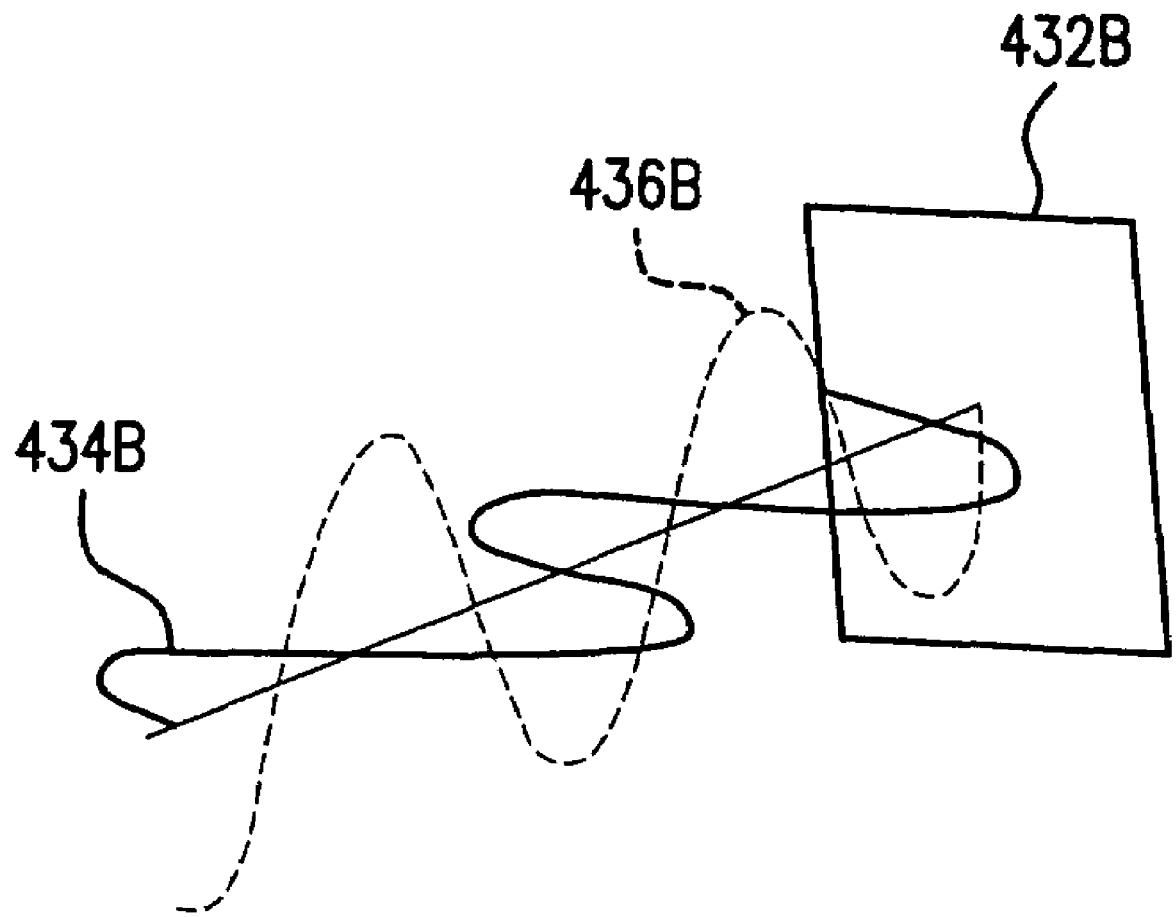
FIG. 4B illustrates the workings of a reflective liquid crystal display, according to an embodiment of the present invention.

An RLCD chip works as is depicted in FIG. 4B. For example, the LC material in an RLCD chip may have properties such that if no voltage is applied to RLCD chip 432B, the polarity of an incident polarized light beam wave 434B changes (i.e., "rotates") ninety degrees (90°). Thus, transmitted polarized light beam wave 436B is ninety degrees out of phase with respect to incident polarized light beam wave 434B. Alternatively, application of a voltage to RLCD chip 432B may not cause the polarity of polarized light beam wave 434A to rotate ninety degrees, thereby allowing light beam wave 434A to simply reflect from the RLCD with the same polarity. At voltages in-between, however, the polarization of the light is partly rotated and elliptically polarized. Alternatively, the LC material may have opposite properties such that if no voltage is applied, the polarity does not change, and if a voltage is applied, the polarity changes 90degrees.

Referring again to FIG. 3, in maskless optical writing system 300, a light source 302 outputs a light beam 304. Light beam 304 is directed toward polarizing beam splitter 326. Polarizing beam splitter 326 reflects a polarized beam 328 toward pattern generator 306. Polarizing beam splitter 326 can be any polarizing dichroic mirror as known in the art. It will be appreciated by those skilled in the art that a polarized beam 305 will pass through polarizing beam splitter 326 with the opposite polarity as polarized beam 328 and be lost from the system.

The RLCD array of pattern generator 306 comprises a plurality of RLCD chips. Each pixel of each RLCD chip is provided with a voltage corresponding to instructions supplied by control signal 208. Pattern generator 306 reflects resulting light beams 316 back toward polarizing beam splitter 326. As with maskless optical writing system 200, the intensity of the resulting exposure on substrate 124 depends indirectly on the voltage supplied to each pixel and the resulting polarization modulation of the output light beams.

In one embodiment of the present invention, the liquid crystal material of the RLCD array has properties such that when no voltage is supplied to a pixel, the polarity of resulting reflected light beam 316 from that pixel is rotated by ninety degrees. Reflected light beam 316 will then be at the correct polarity to pass directly through polarizing beam splitter 326. In this embodiment, when a voltage is supplied to a pixel (e.g., a "no-polarity-change" voltage), the polarity of resulting reflected light beam 316 from that pixel does not change and will again reflect from polarizing beam splitter 326 as beam 317 and be lost from the system. At voltages supplied to pixels that are between zero and the "no-polarity-change" voltage, the polarization of resulting reflected beams 316 from those pixels is partly rotated and elliptically polarized, allowing some light to pass through polarizing beam splitter 326, and therefore allowing greyscale levels to occur in reflected light beams 316.

In another embodiment of the present invention, the liquid crystal material of the RLCD array has properties such that when a certain voltage is supplied to a pixel (e.g., a "90-degree-polarity-change" voltage), the polarity of the resulting reflected light beam 316 from that pixel is rotated by ninety degrees. Reflected light beam 316 will then be at the correct polarity to pass directly through polarizing beam splitter 326. In this embodiment, when no voltage is supplied to a pixel, the polarity of resulting reflected light beam 316 from that pixel does not change and will again reflect from polarizing beam splitter 326 as beam 317 and be lost from the system. At voltages supplied to pixels that are between zero and the "90-degree-polarity-change" voltage, the polarization of resulting reflected beams 316 from those pixels is partly rotated and elliptically polarized, allowing some light to pass through polarizing beam splitter 326, and therefore allowing greyscale levels to occur in light beams 316.

In maskless optical writing system 300, resulting reflected light beam 316 is minimized by reduction optics 118. Reduction optics 118 comprises a plurality of lenses. Reduction optics 118 can encompass any suitable reduction optics for this purpose, as is to be appreciated by those skilled in the art. Minimized light beam 320 is then projected onto substrate 124 held by substrate stage 122. The intensity of the exposure on substrate 124 depends indirectly on the amount of voltage applied to each corresponding pixel of pattern generator 306, as previously described.

In embodiments of the present invention, pattern generators 206/306 are compatible with 157 nm illumination to 248 nm illumination, with 193 nm illumination preferred.

A "slit" area defines the area of projection onto a substrate. The size of a slit area is related to magnification, chip size, and the number of chips arrayed.

According to embodiments of the present invention, multiple chips are laid out in an array. For a high resolution wafer application, according to embodiments of the present invention, a slit area of approximately 8 mm by 22 mm is preferably used, which involves an array of chips. For wafer applications, this area can be as small as 4 mm by 12 mm or as large as 16 mm by 48 mm, depending on the optics design. However, this area can be smaller or larger than this range, depending on the application in which the invention is used. For example, the slit area for pattern generators used in a flat panel application could be as large as 8 cm by 22 cm or larger. Pattern generators used for projection televisions or cinema screens can cover even larger slit areas, used for screens of 50 feet or larger, for example. For large applications such as these, however, the pixel size will be large.

In embodiments of the present invention, maskless optical writing systems 200/300 can generate pixel sizes on a substrate from 20 nm to 1.5 mm, with a preferred size of approximately 50 nm. According to embodiments of the present invention, reduction optics 118 can minimize a pattern image by a magnification range of 0.005× to 350×, with a magnification of 200× preferred.

In embodiments of the present invention, light source 202/302 is a pulsed excimer laser. Using this laser, individual voltage levels of individual pixels are changed between laser pulses. In embodiments of the present invention, the light source 202/302 provides polarized light.

As previously stated, controller 210 comprises a pattern information manipulator 230. Pattern information manipulator 230 decodes pattern information received from data stream 112, and assigns the pattern information data on a pixel-by-pixel basis. According to an embodiment of the present invention, the pattern information manipulator 230 assigns greyscale values for each pixel. Embodiments of pattern information manipulator 230 can comprise hardware, software, or a combination of hardware and software.

Figure 5:
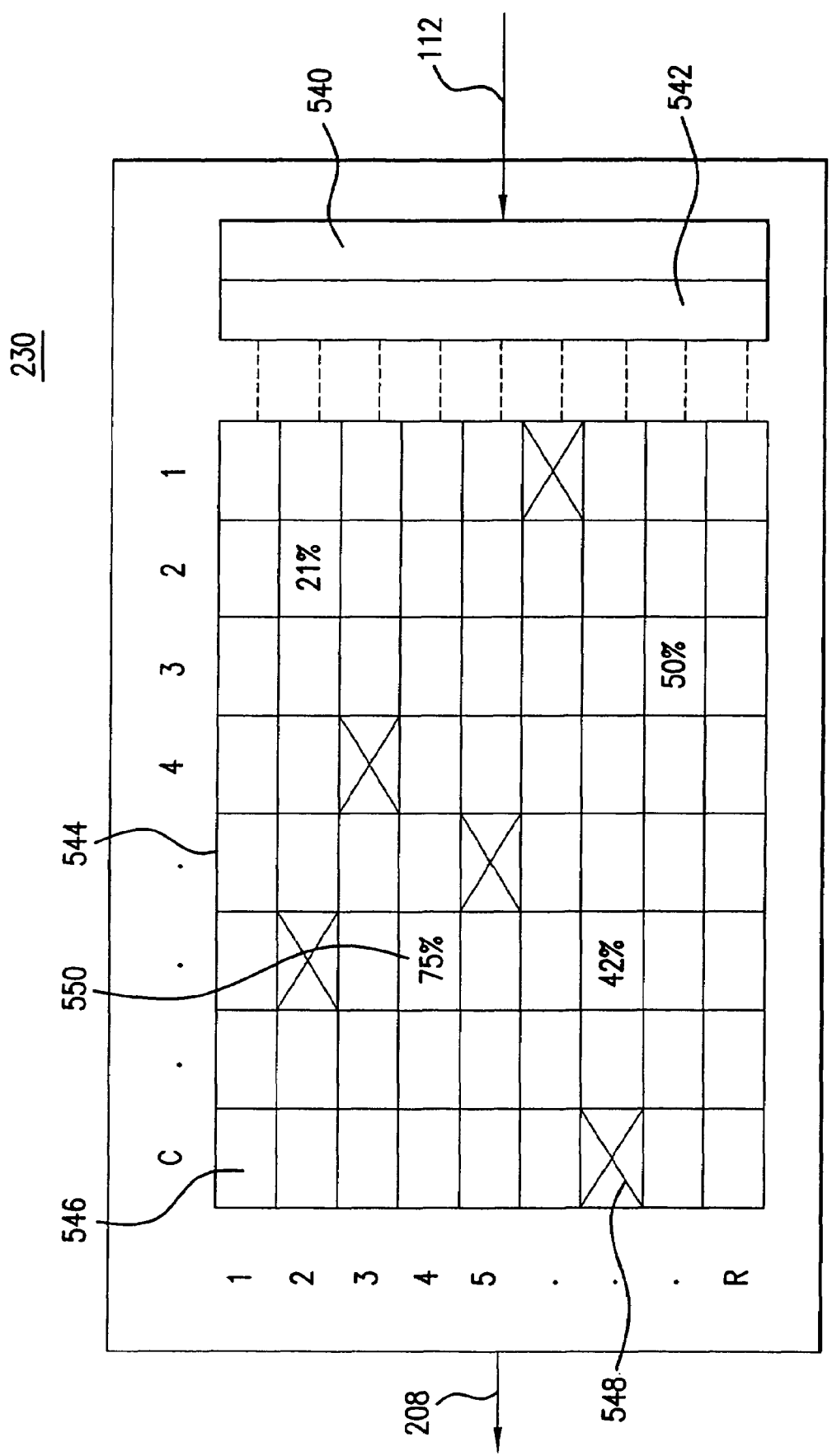
FIG. 5 is an exemplary illustration of a pattern generator controller data manipulator, according to an embodiment of the present invention.

FIG. 5 illustrates pattern information manipulator 230 in more detail.

Data stream 112, containing pattern information enters pattern information manipulator 230 and is decoded at a decoder 540. Pixel addresses are generated at an address generator 542. Instructions for each pixel are stored in a memory 544 as a pixel "matrix" in a row-by-column manner. For example, a pixel can correspond with an instruction to apply a "maximum" voltage, as depicted by pixel address 546. Alternatively, a pixel can correspond with an instruction to apply no voltage, as depicted by pixel address 548. A greyscale level of exposure can alternatively be assigned to a pixel by assigning a voltage that is in-between these two levels. For example, exposure at 75% is assigned to pixel address 550. It will be appreciated by those skilled in the art that some linearity correction is needed within the pattern information manipulator 230 of controller 210 to ensure that the greyscale effect is linear as compared to the voltages applied.

Figure 6:
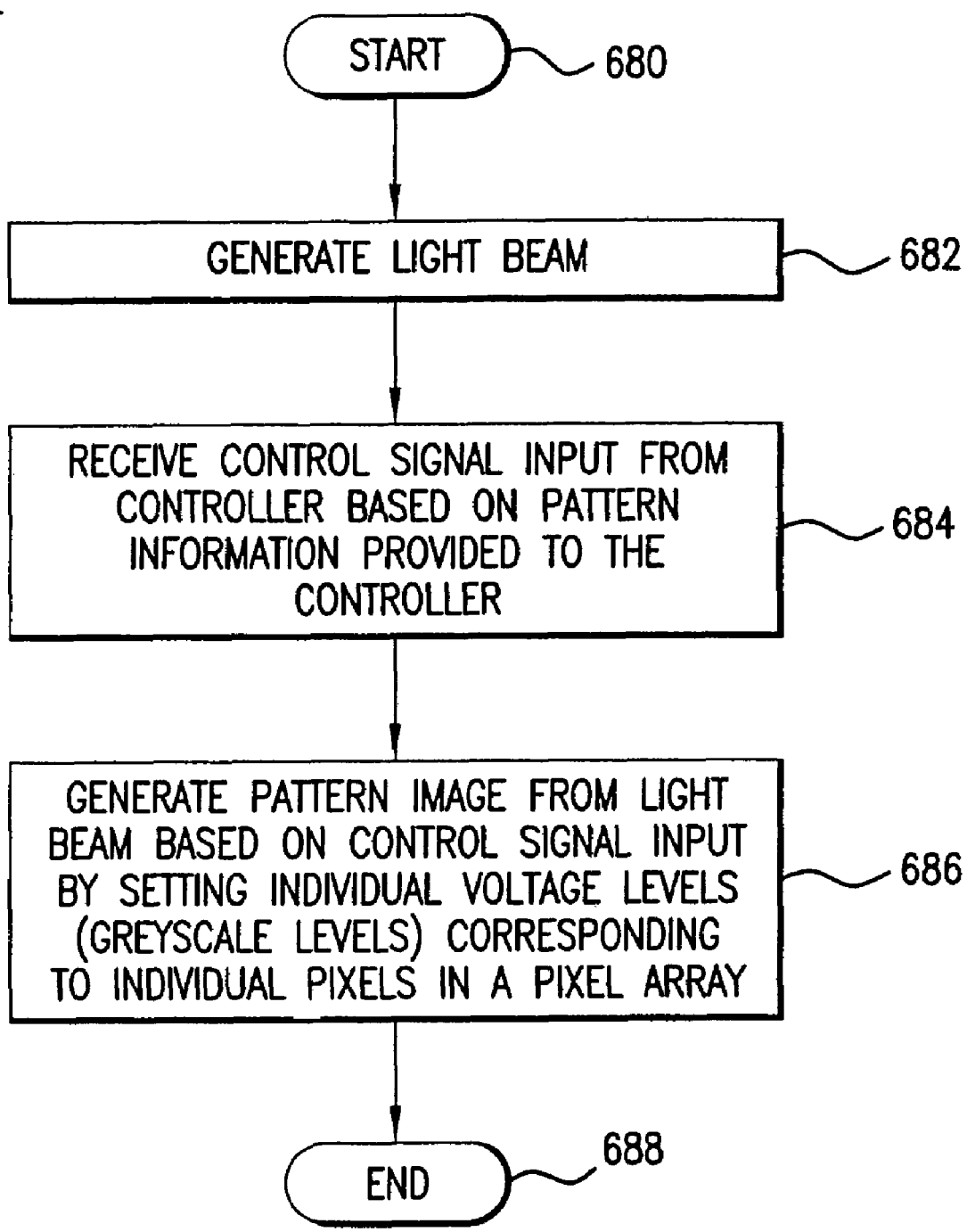
FIG. 6 is a flowchart illustrating a method of generating a maskless pattern, according to an embodiment of the present invention.

A method 600 of generating a maskless pattern, according to an embodiment of the present invention, is illustrated in FIG. 6. The method starts at step 680 and immediately continues at step 682. In step 682, a light beam is generated. In step 684, a control signal input is received from a controller based on pattern information provided to the controller. In step 686, a pattern image is generated from the light beam based on the control signal input. In an embodiment, the pattern image is generated by setting individual voltage levels (i.e., greyscale levels) corresponding to individual pixels in a pixel array. Method 600 ends at step 688.

Figure 7A:
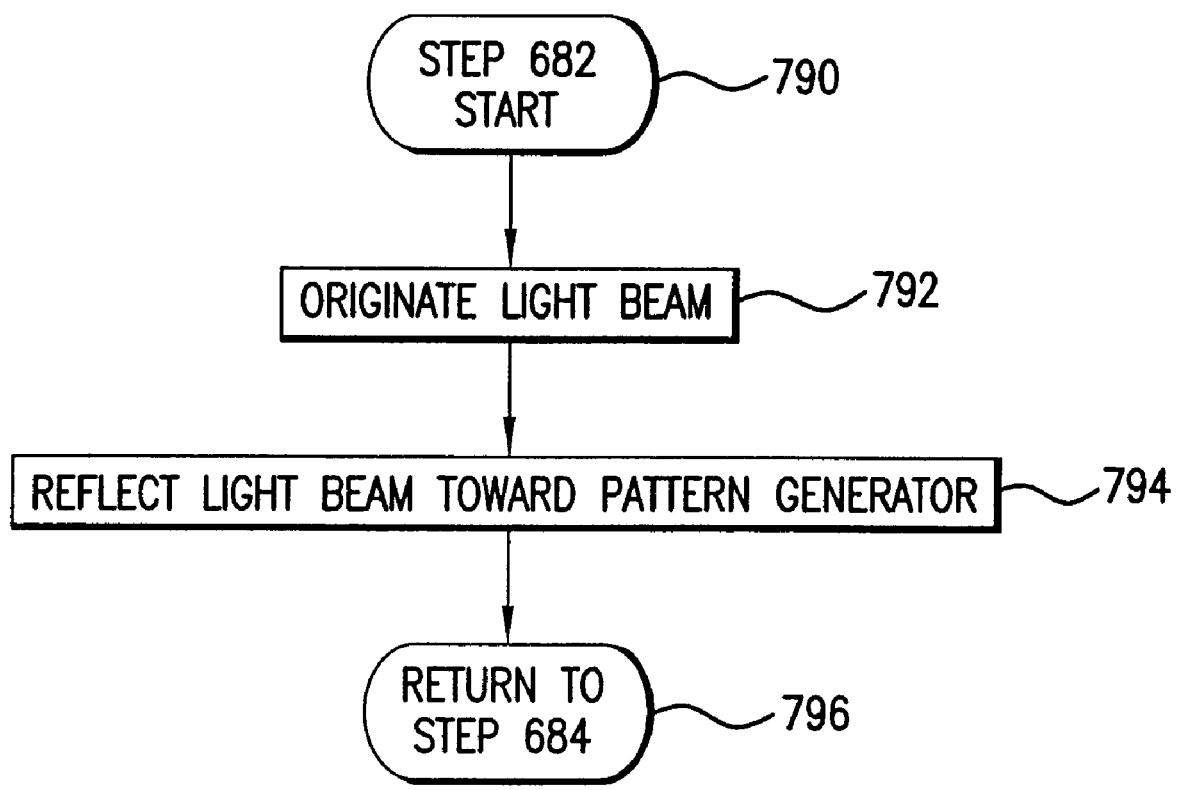
FIGS. 7A and 7B are flowcharts illustrating step 682 of the method illustrated in FIG. 6, according to embodiments of the present invention.

In one embodiment of the present invention, step 682 of method 600 is carried out as depicted in FIG. 7A. Step 682 starts at step 790 and immediately continues to step 792. In step 792, a light beam is generated. In step 794, the light beam is reflected toward a pattern generator. The reflection can be accomplished by any beam splitter. In an embodiment, a polarized beam splitter is used. In step 796, the method returns to step 684 of method 600.

Figure 7B:
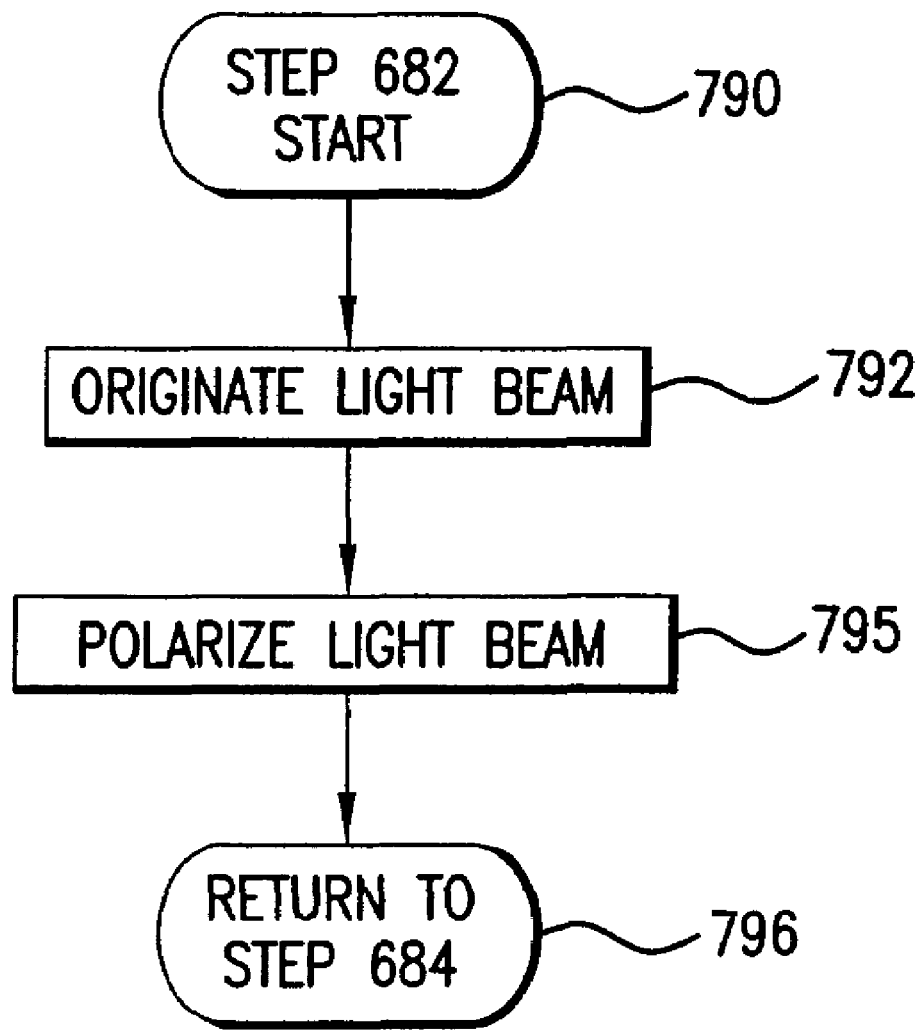

In another embodiment of the present invention, step 682 of method 600 is carried out as depicted in FIG. 7B. Step 682 starts at step 790 and immediately continues to step 792. In step 792, a light beam is generated. In step 795, the light beam is polarized. Polarization of the light beam can be accomplished using any polarizer as is recognized by those skilled in the art. In step 796, the method returns to step 684 of method 600.

Figure 8:
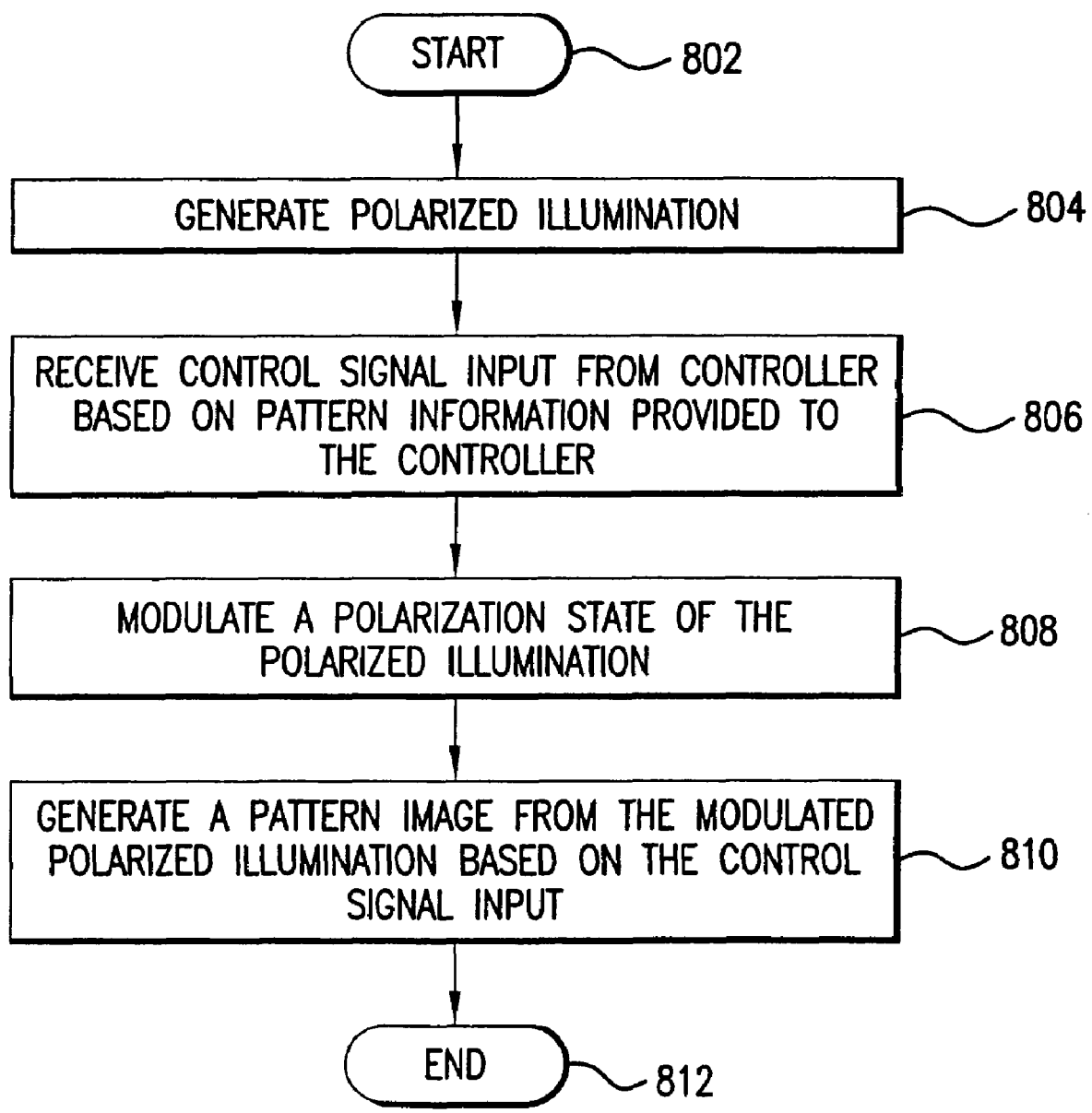
FIG. 8 is a flowchart illustrating a method of generating a maskless pattern, according to an embodiment of the present invention.

A method 800 of generating a maskless pattern, according to an embodiment of the present invention, is illustrated in FIG. 8. The method starts at step 802 and immediately continues at step 804. In step 804, a polarized illumination is generated. In step 806, a control signal input is received from a controller based on pattern information provided to the controller. In step 808, a polarization state of the polarized illumination is modulated. In step 810, a pattern image is generated from the modulated polarized illumination based on the control signal input. Method 800 ends at step 812.

Figure 9:
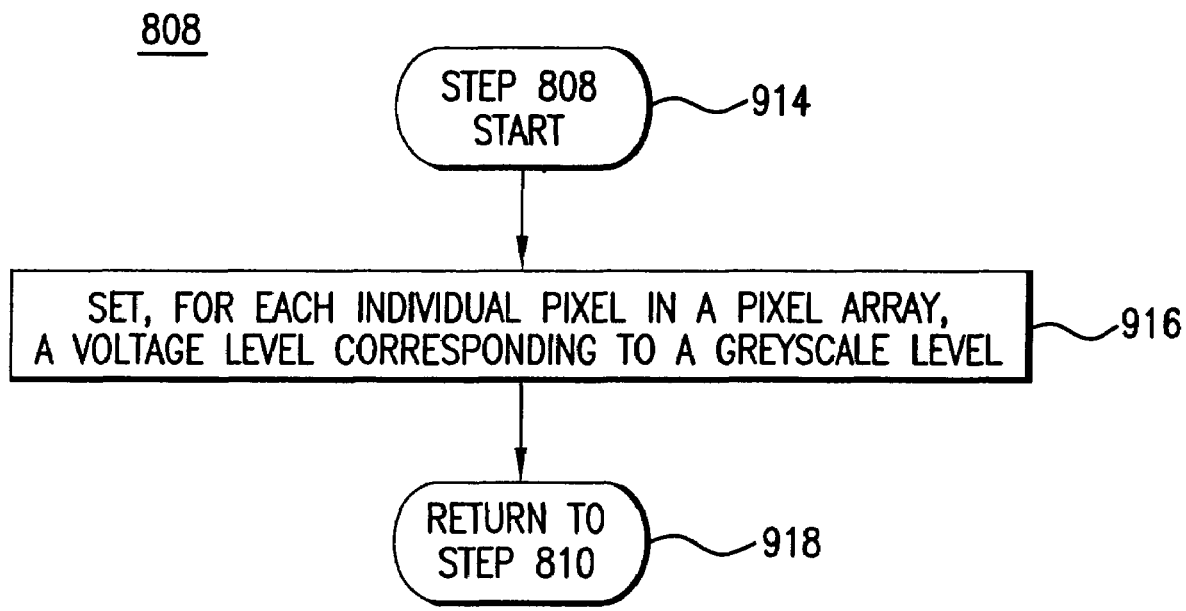
FIG. 9 is a flowchart illustrating step 808 of the method illustrated in FIG. 8, according to an embodiment of the present invention.

In one embodiment of the present invention, step 808 of method 800 is carried out as depicted in FIG. 9. Step 808 starts at step 914 and immediately continues to step 916. In step 916, a voltage level corresponding to a greyscale level (including black and white) is set for each individual pixel in a pixel array. In step 918, the method returns to step 810 of method 800.

Figure 10:
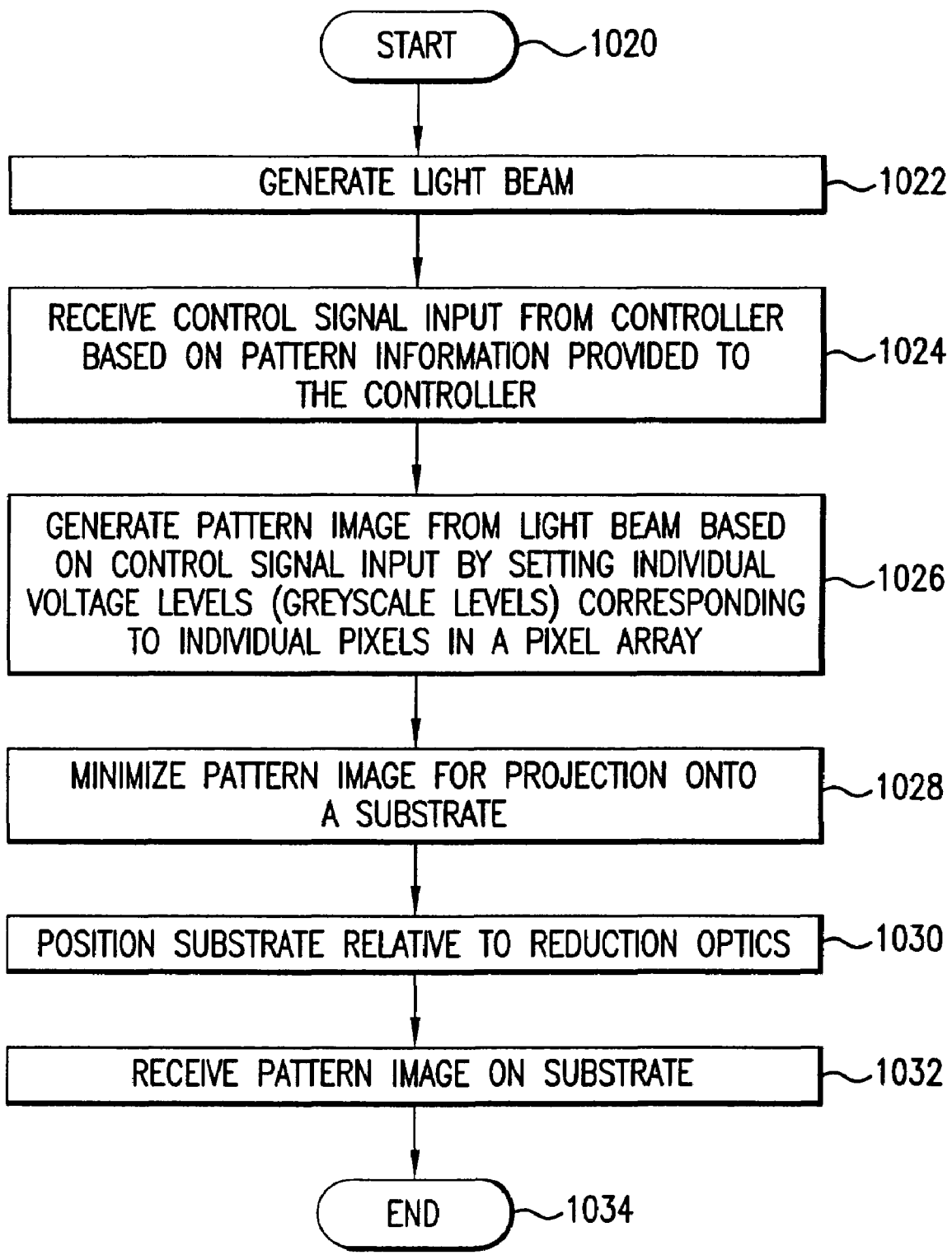
FIG. 10 is a flowchart illustrating a method of performing maskless lithography, according to an embodiment of the present invention.

A method 1000 of performing maskless lithography, according to an embodiment of the present invention, is illustrated in FIG. 10. The method starts at step 1020 and immediately continues at step 1022. In step 1022, a light beam is generated. In step 1024, a control signal input is received from a controller based on pattern information provided to the controller. In step 1026, a pattern image is generated from the light beam based on the control signal input. In an embodiment, the pattern image is generated by setting individual voltage levels (i.e., greyscale levels) corresponding to individual pixels in a pixel array. In step 1028, the pattern image is minimized by reduction optics for projection onto a substrate. In step 1030, the substrate is positioned relative to the reduction optics. In step 1032, the pattern image is received on the substrate. Method 1000 ends at step 1034.

Figure 11A:
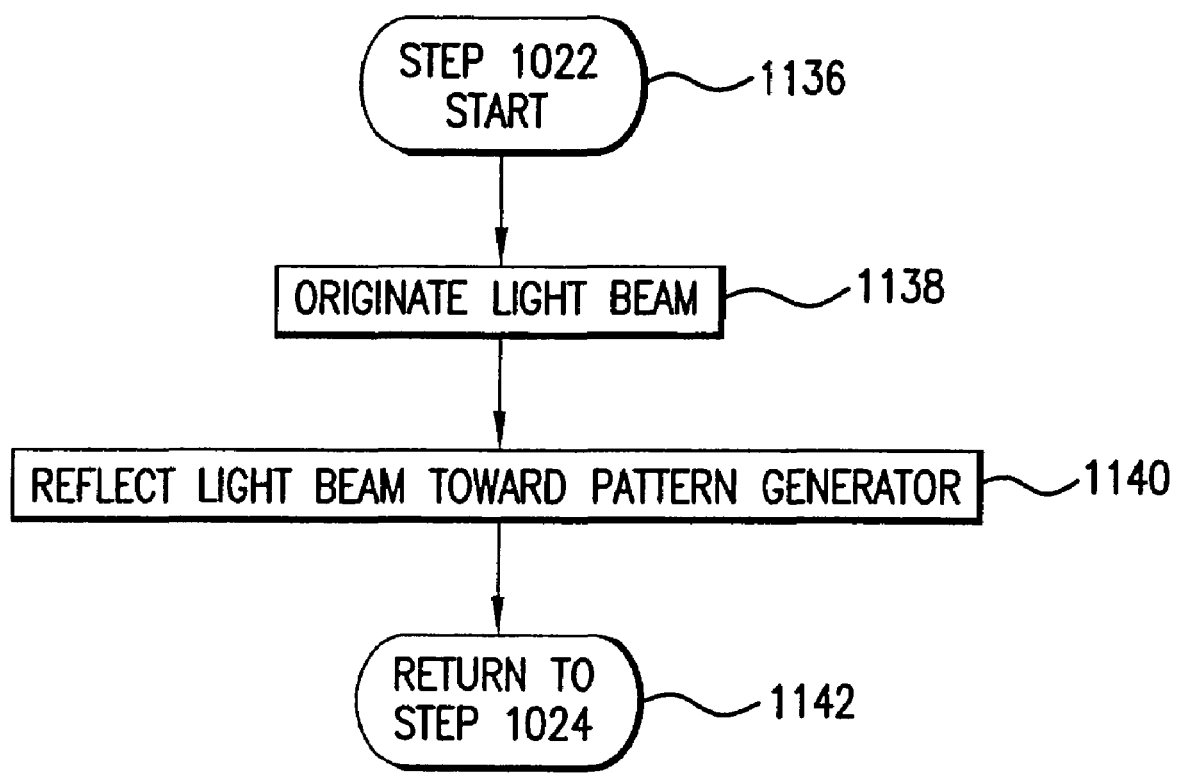
FIGS. 11A and 11B are flowcharts illustrating step 1022 of the method illustrated in FIG. 10, according to embodiments of the present invention.

In one embodiment of the present invention, step 1022 of method 1000 is carried out as depicted in FIG. 11A. Step 1022 starts at step 1136 and immediately continues to step 1138. In step 1138, a light beam is generated. In step 1140, the light beam is reflected toward a pattern generator. The reflection can be accomplished by any beam splitter, as is recognized by those skilled in the art. In an embodiment, a polarized beam splitter is used. In step 1142, the method returns to step 1024 of method 1000.

Figure 11B:
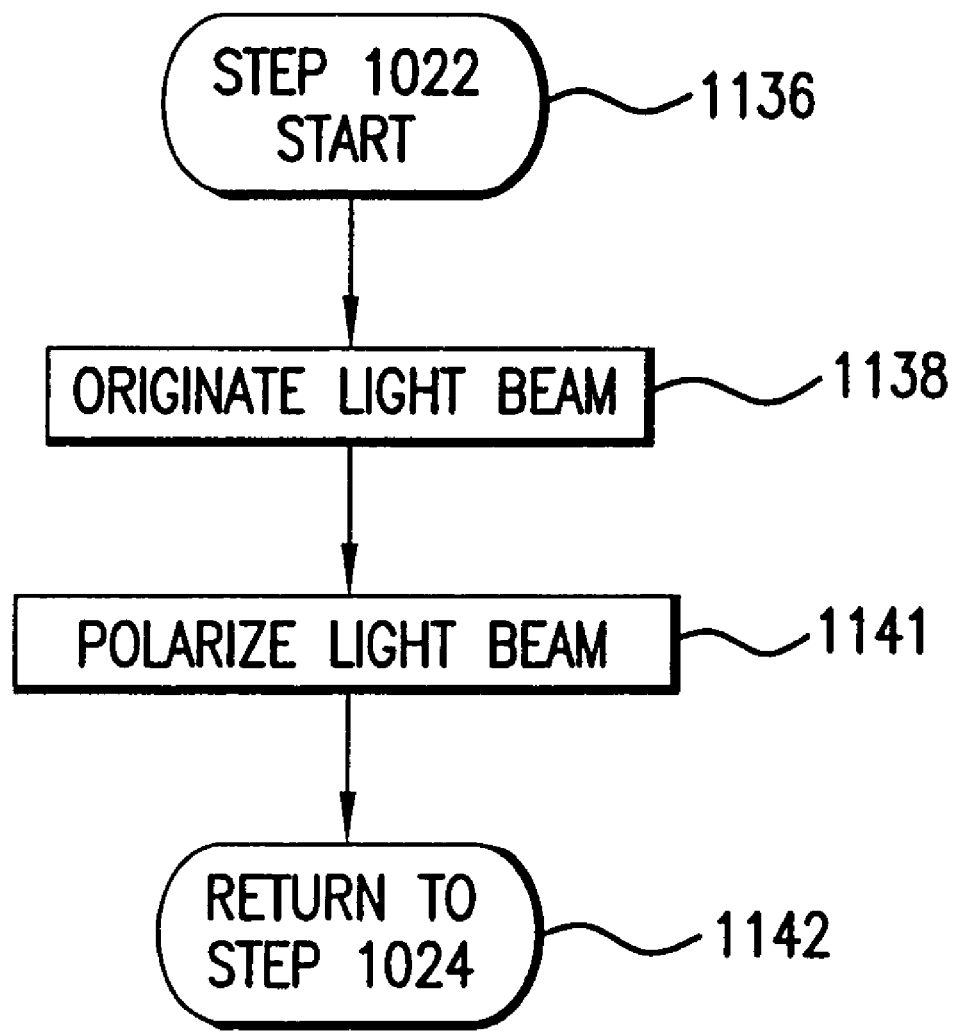

In another embodiment of the present invention, step 1022 of method 1000 is carried out as depicted in FIG. 11B. Step 1022 starts at step 1136 and immediately continues to step 1138. In step 1138, a light beam is generated. In step 1141, the light beam is polarized. Polarization of the light beam can be accomplished using any polarizer, as is recognized by those skilled in the art. In step 1142, the method returns to step 1024 of method 1000.

Figure 12:
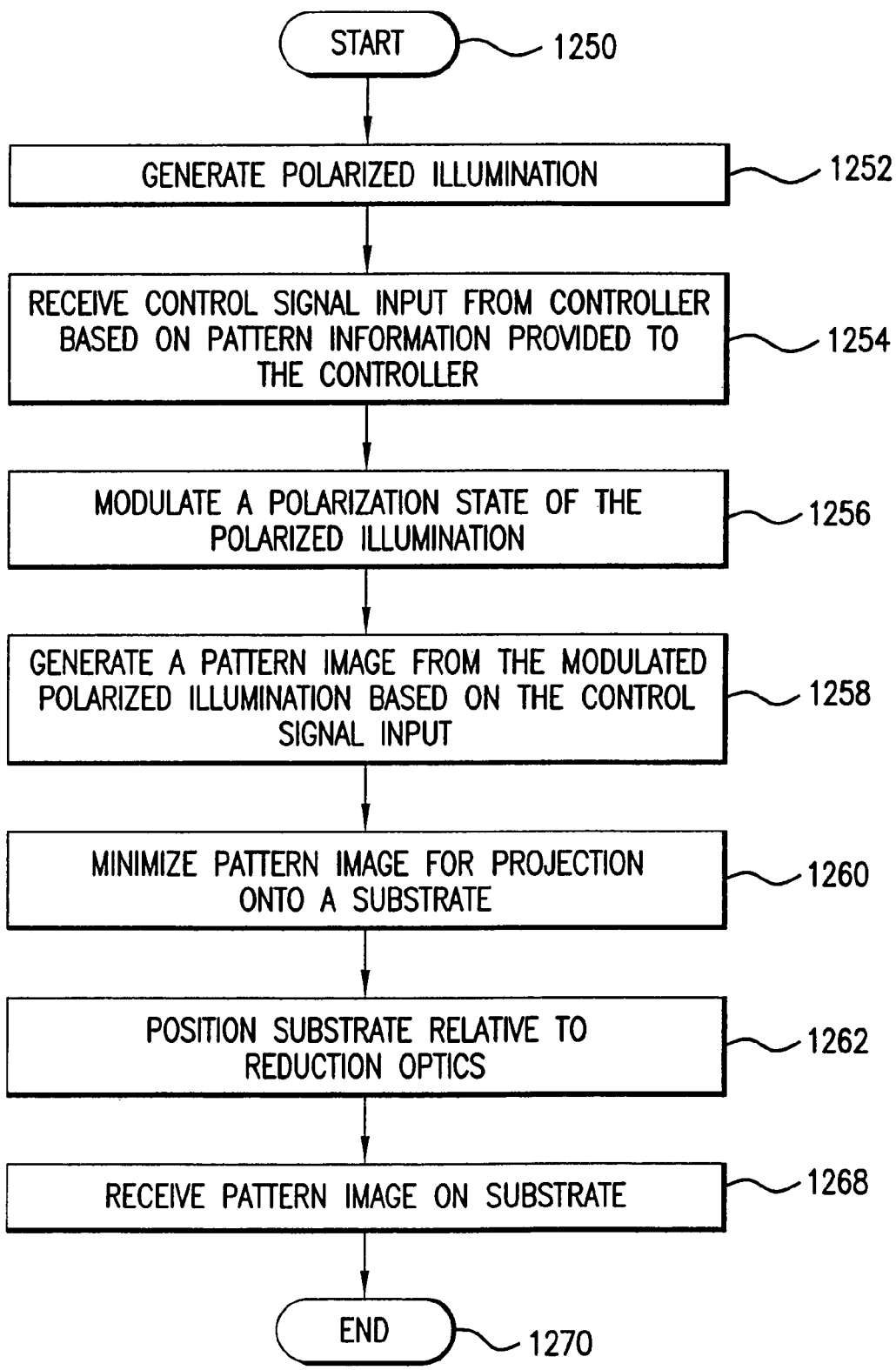
FIG. 12 is a flowchart illustrating a method of performing maskless lithography, according to an embodiment of the present invention.

A method 1200 of performing maskless lithography, according to an embodiment of the present invention, is illustrated in FIG. 12. The method starts at step 1250 and immediately continues at step 1252. In step 1252, a polarized illumination is generated. In step 1254, a control signal input is received from a controller based on pattern information provided to the controller. In step 1256, a polarization state of the polarized illumination is modulated. In step 1258, a pattern image is generated from the modulated polarized illumination based on the control signal input. In step 1260, the pattern image is minimized by reduction optics for projection onto a substrate. In step 1262, the substrate is positioned relative to the reduction optics. In step 1268, the pattern image is received on the substrate. Method 1200 ends at step 1270.

Figure 13:
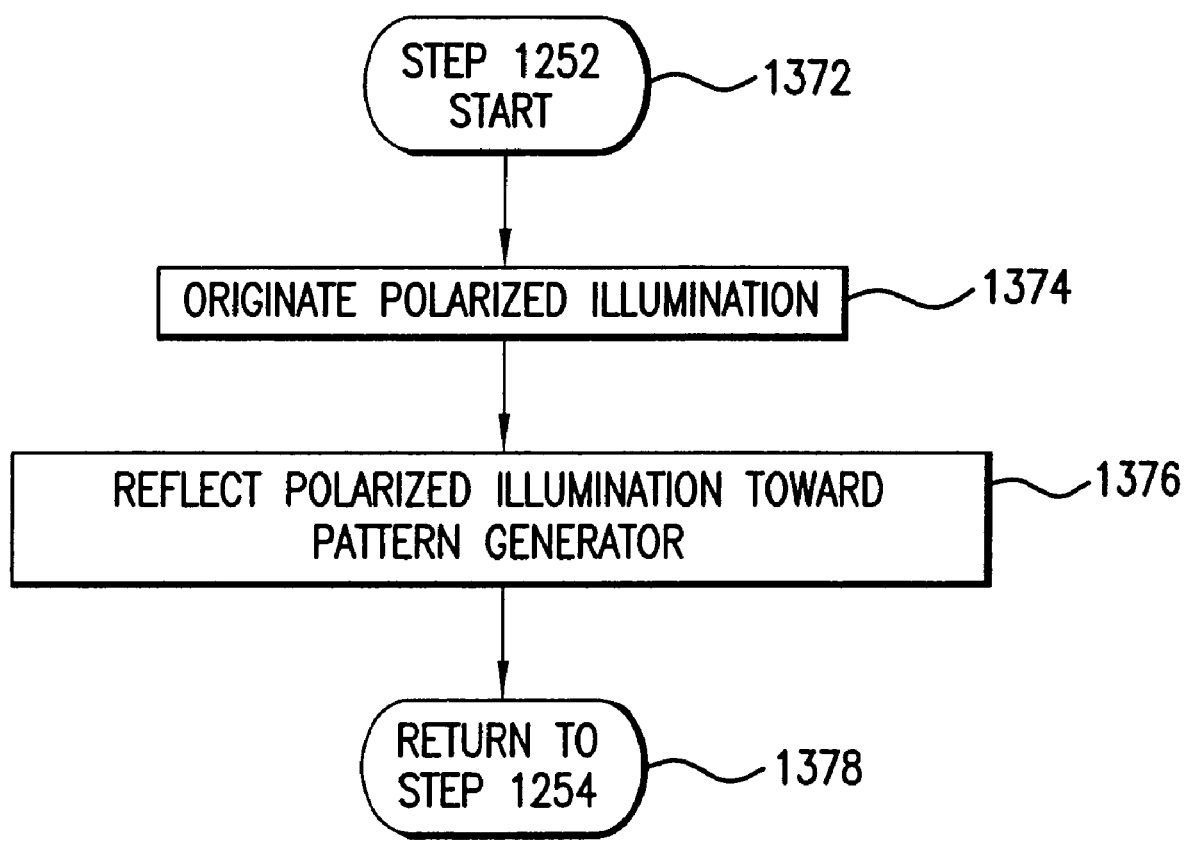
FIG. 13 is a flowchart illustrating step 1252 of the method illustrated in FIG. 12, according to an embodiment of the present invention.

In one embodiment of the present invention, step 1252 of method 1200 is carried out as depicted in FIG. 13. Step 1252 starts at step 1372 and immediately continues to step 1374. In step 1374, a polarized illumination is generated. In step 1376, the polarized illumination is reflected toward a pattern generator. The reflection can be accomplished by any beam splitter. In an embodiment, a polarized beam splitter is used. In step 1378, the method returns to step 1254 of method 1200.

Figure 14:
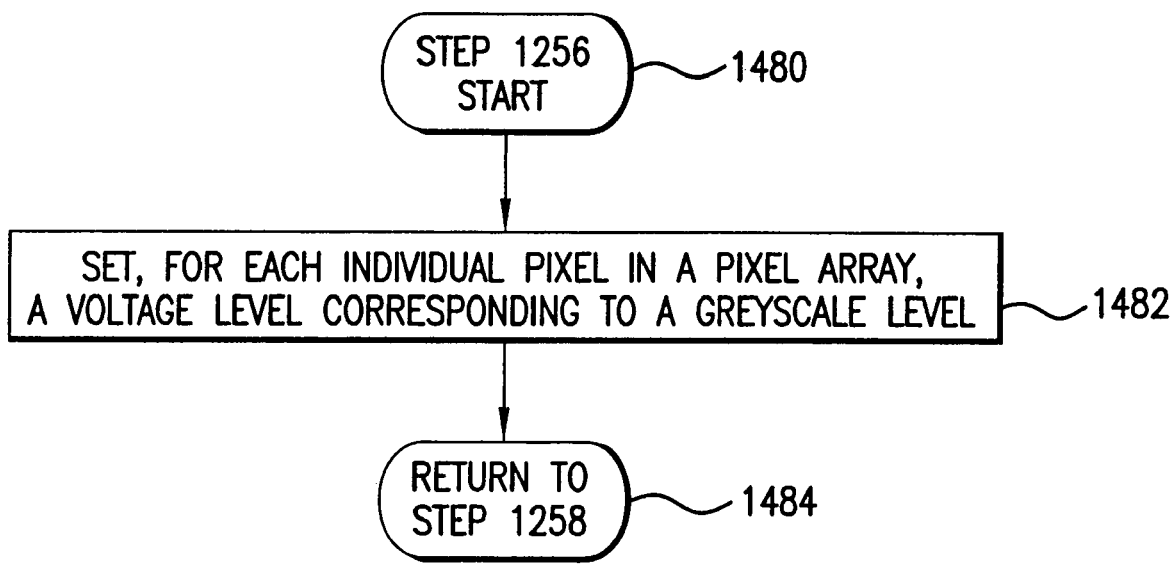
FIG. 14 is a flowchart illustrating step 1256 of the method illustrated in FIG. 12, according to an embodiment of the present invention.

In one embodiment of the present invention, step 1256 of method 1200 is carried out as depicted in FIG. 14. Step 1256 starts at step 1480 and immediately continues to step 1482. In step 1482, a voltage level corresponding to a greyscale level (including black and white) is set for each individual pixel in a pixel array. In step 1484, the method returns to step 1258 of method 1200.

Figure 15:
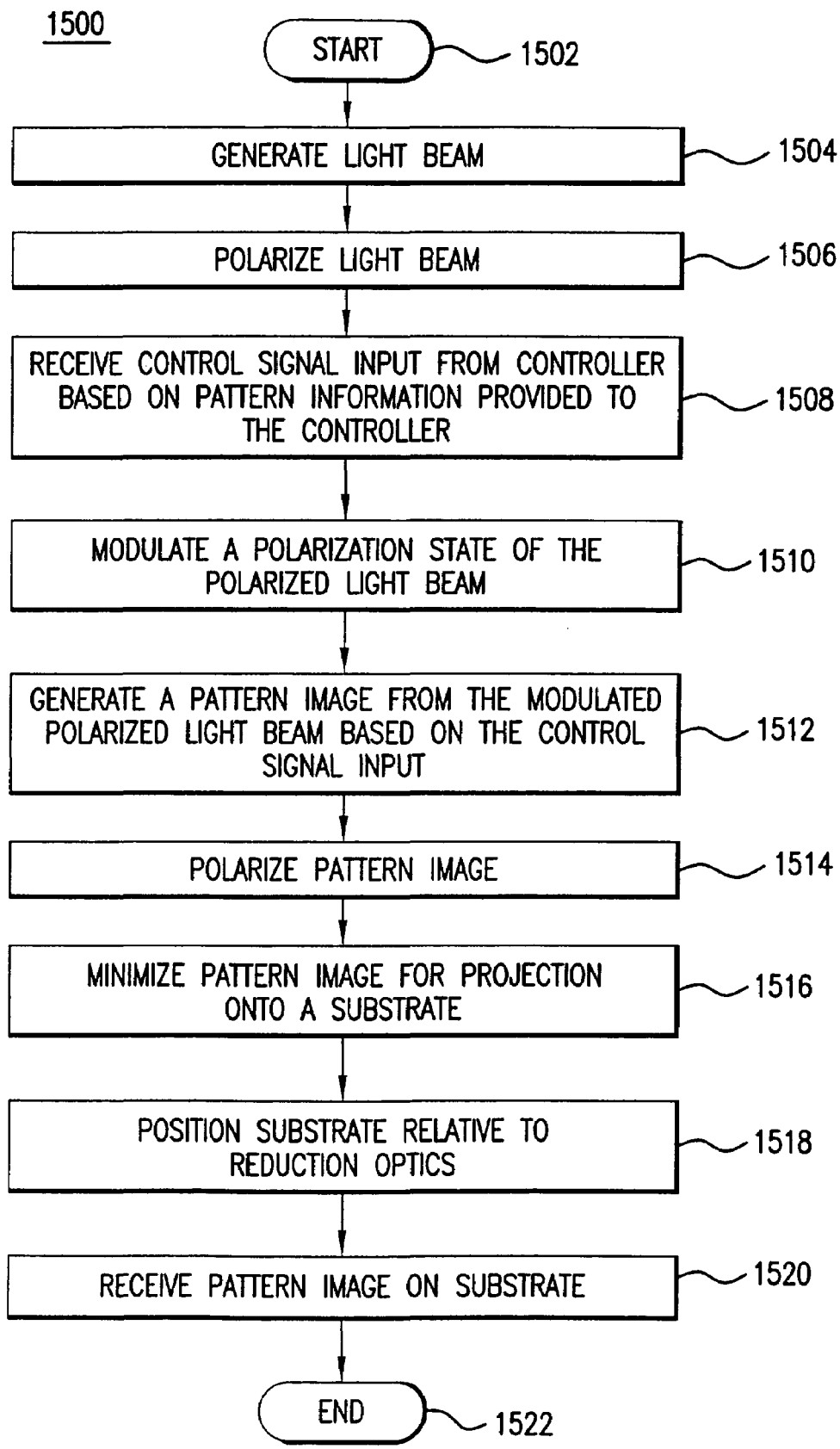
FIGS. 15 and 16 are flowcharts illustrating methods of performing maskless lithography, according to embodiments of the present invention.

A method 1500 of performing maskless lithography, according to an embodiment of the present invention, is illustrated in FIG. 15. The method starts at step 1502 and immediately continues at step 1504. In step 1504, a light beam is generated. In step 1506, the light beam is polarized. In step 1508, a control signal input is received from a controller based on pattern information provided to the controller. In step 1510, a polarization state of the polarized light beam is modulated. In step 1512, a pattern image is generated from the modulated polarized light beam based on the control signal input. In an embodiment, the pattern image is generated by setting individual voltage levels (i.e., greyscale levels) corresponding to individual pixels in a pixel array. In step 1514, the pattern image is polarized. In step 1516, the pattern image is minimized by reduction optics for projection onto a substrate. In step 1518, the substrate is positioned relative to the reduction optics. In step 1520, the pattern image is received on the substrate. Method 1500 ends at step 1522.

Figure 16:
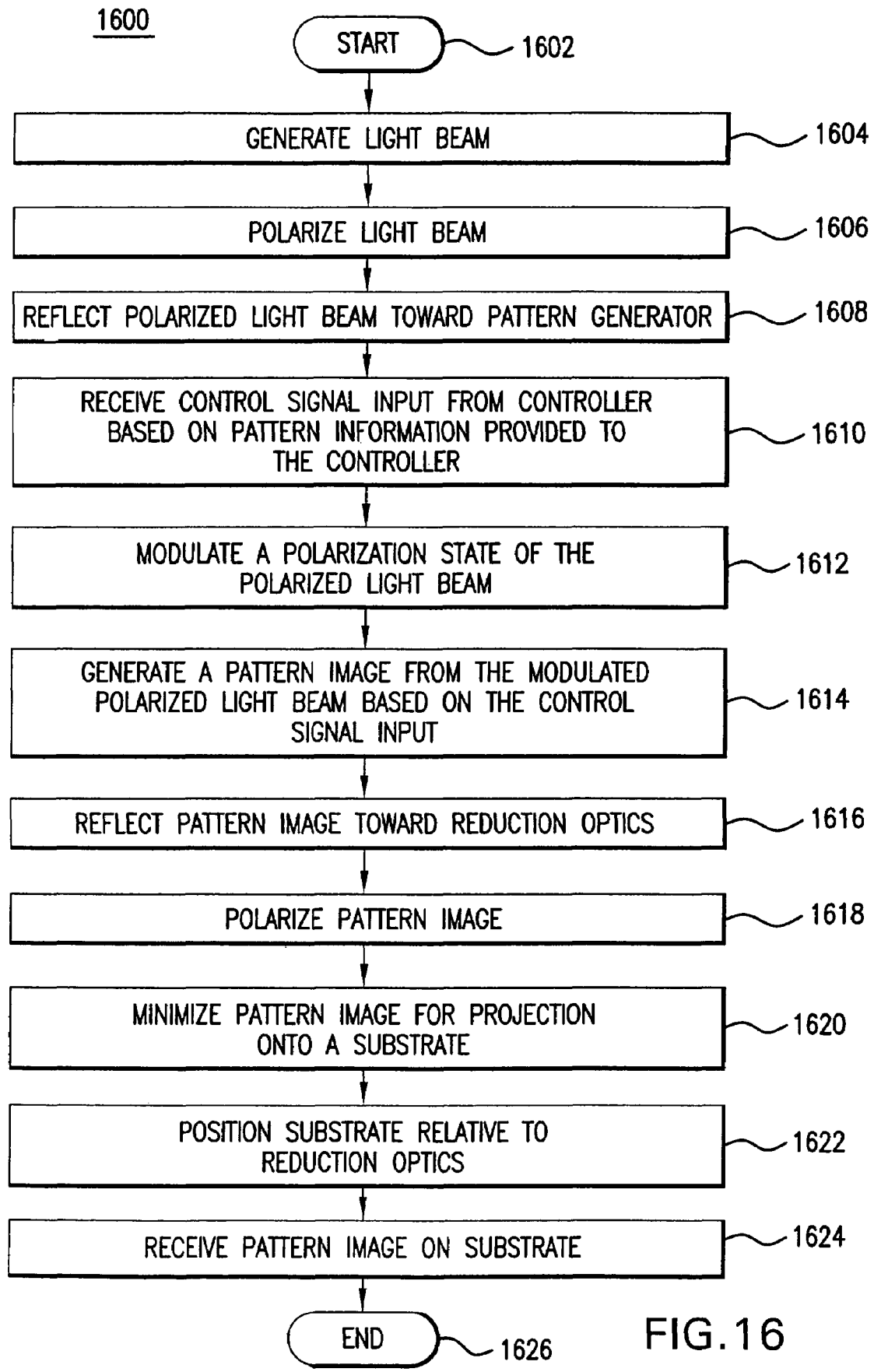

A method 1600 of performing maskless lithography, according to an embodiment of the present invention, is illustrated in FIG. 16. The method starts at step 1602 and immediately continues at step 1604. In step 1604, a light beam is generated. In step 1606, the light beam is polarized. In step 1608, the polarized light beam is reflected toward a pattern generator. In step 1610, a control signal input is received from a controller based on pattern information provided to the controller. In step 1612, a polarization state of the polarized light beam is modulated. In step 1614, a pattern image is generated from the modulated polarized light beam based on the control signal input. In an embodiment, the pattern image is generated by setting individual voltage levels (i.e., greyscale levels) corresponding to individual pixels in a pixel array. In step 1616, the pattern image is reflected toward reduction optics. In step 1618, the pattern image is polarized.

In step 1620, the pattern image is minimized by reduction optics for projection onto a substrate. In step 1622, the substrate is positioned relative to the reduction optics. In step 1624, the pattern image is received on the substrate. Method 1600 ends at step 1626.

One advantage of the present invention is that it can be used as a phase shift mask. By applying a voltage over more than one cycle of light, a phase shift occurs that imparts useful characteristics similar to a phase shift mask as understood by those skilled in the art. To use the present invention as a phase shift mask, one changes the voltage past the point where the polarization has rotated 90 degrees. This pixel-by-pixel phase interference has the same effect as a phase shift mask, improving the resolution of the system.

Another advantage of the present invention is that a pattern image can be easily moved by shifting the voltage levels applied to each pixel depending on exactly where the pattern needs to be placed. The placement of the pattern image is shifted when the individual voltage levels set for corresponding pixels are shifted in one direction by the same number of pixel rows or columns.

A further advantage of the present invention is that greyscaling in the manner described allows the pattern to be easily moved relative to the definition grid. On a substrate, the light from each pixel merges into the light from other pixels. At the edges of a pattern, the light from the edge row of pixels "spills" over and gradually changes from light to dark in a graduated effect. How quickly the transition from light to dark occurs can be controlled by partly turning on the pixels in the transition region. In this way, the light levels of the pixels are manipulated by applying the appropriate voltage levels to "move" an edge of the pattern. This feature of the invention may be used to allow a transition (the gradual change from light to dark) to occur at a boundary that does not correspond to a basic grid boundary. For example, if the pixels are on a 40 nm grid, and it is desired to position the edge of the pattern on a 5 nm grid, the result may be a transition that is not occurring at a location where one of the basic grid boundaries occurs. In order to move a pattern edge away from the basic grid boundary, the light levels of the pixels on either side of that boundary can be manipulated by applying the appropriate voltage levels to those pixels.

Figure 17:
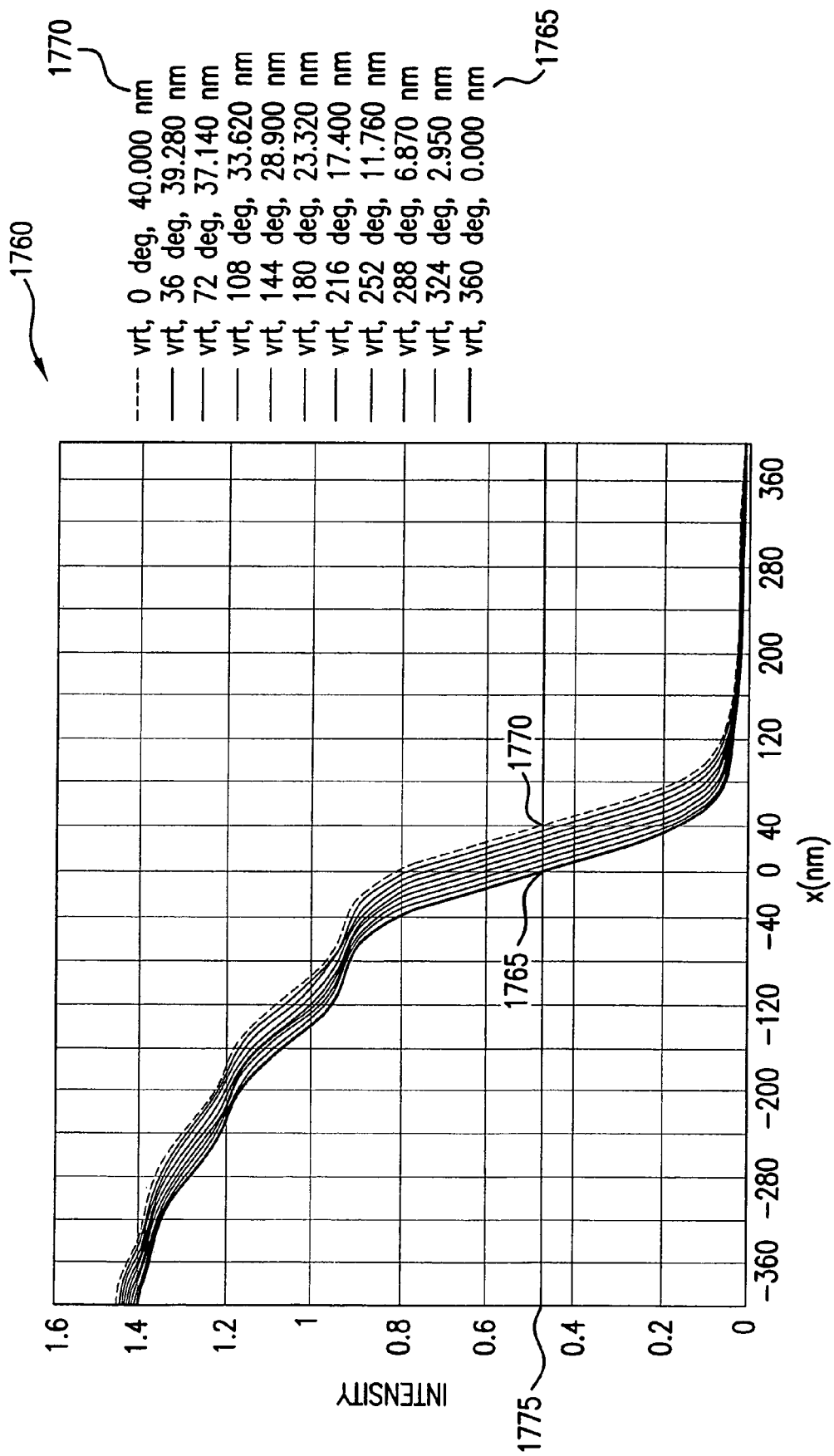
FIG. 17 is a chart illustrating the shifting of an exposed edge through the use of greyscaling, according to an embodiment of the present invention.

The chart of FIG. 17 shows the shifting of an exposed edge through the use of greyscaling as described in connection with the present invention. Chart 1760 shows the plotting of light intensity variation across an exposure edge. At a certain voltage applied to a pixel, the pixel is considered completely "off," as shown by plot 1765. At a different voltage applied to the pixel, the pixel is considered completely "on," as shown by plot 1770. At the same specific level of intensity (shown by dashed line 1775), the distance between the pattern edges when completely "off" (plot 1765) versus completely "on" (plot 1770) is 40 nm, which in this example is the width of the pixel. Varying the voltage level applied to the pixel to a voltage between the two voltage levels for "on" and "off" allow the pattern edge to be located at intermediate positions, as shown by the data plots in-between plot 1765 and 1770.

Figure 18:
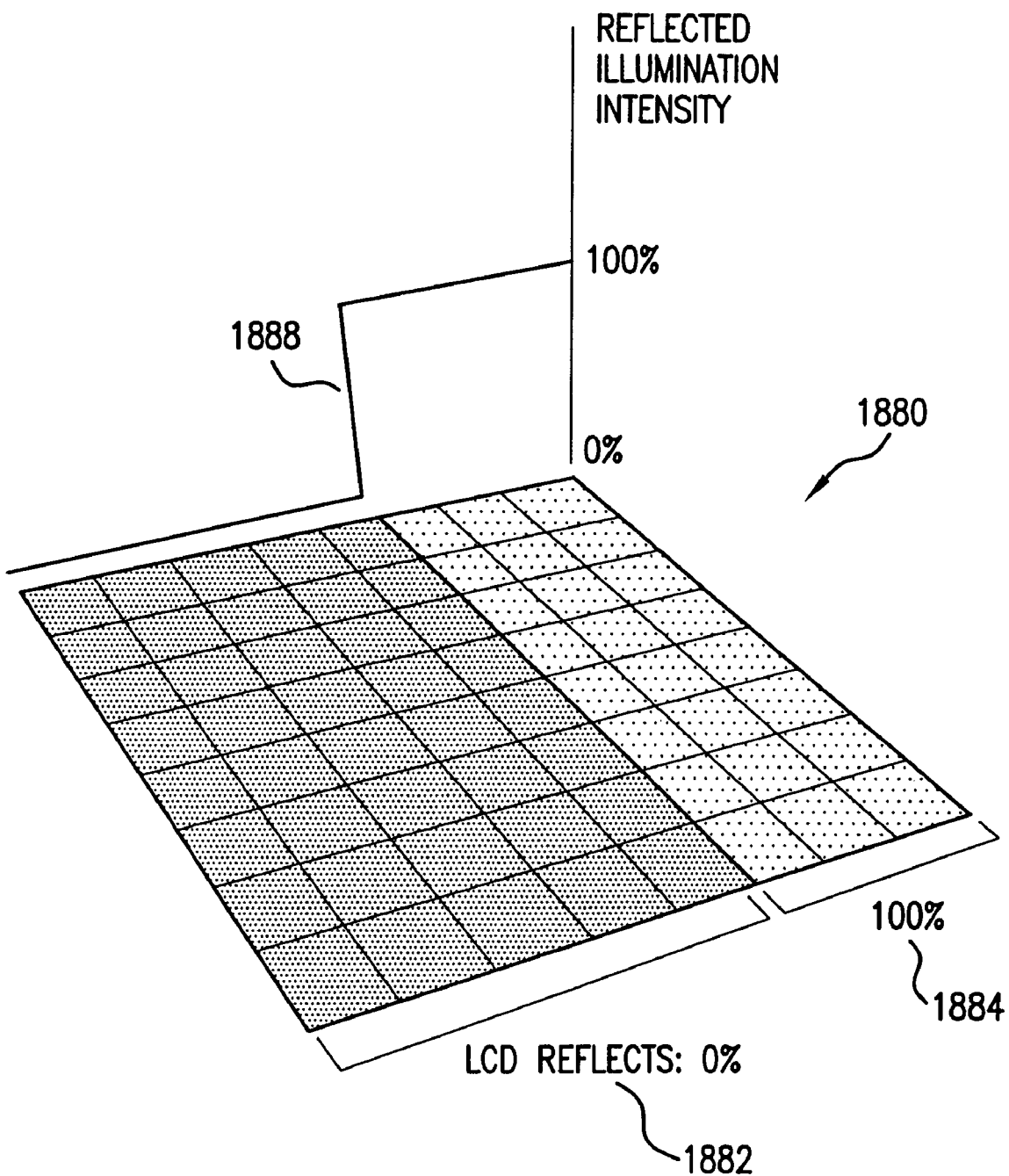
FIGS. 18 and 19 illustrate the shifting of an exposed edge through the use of greyscaling, according to an embodiment of the present invention.
Figure 19:
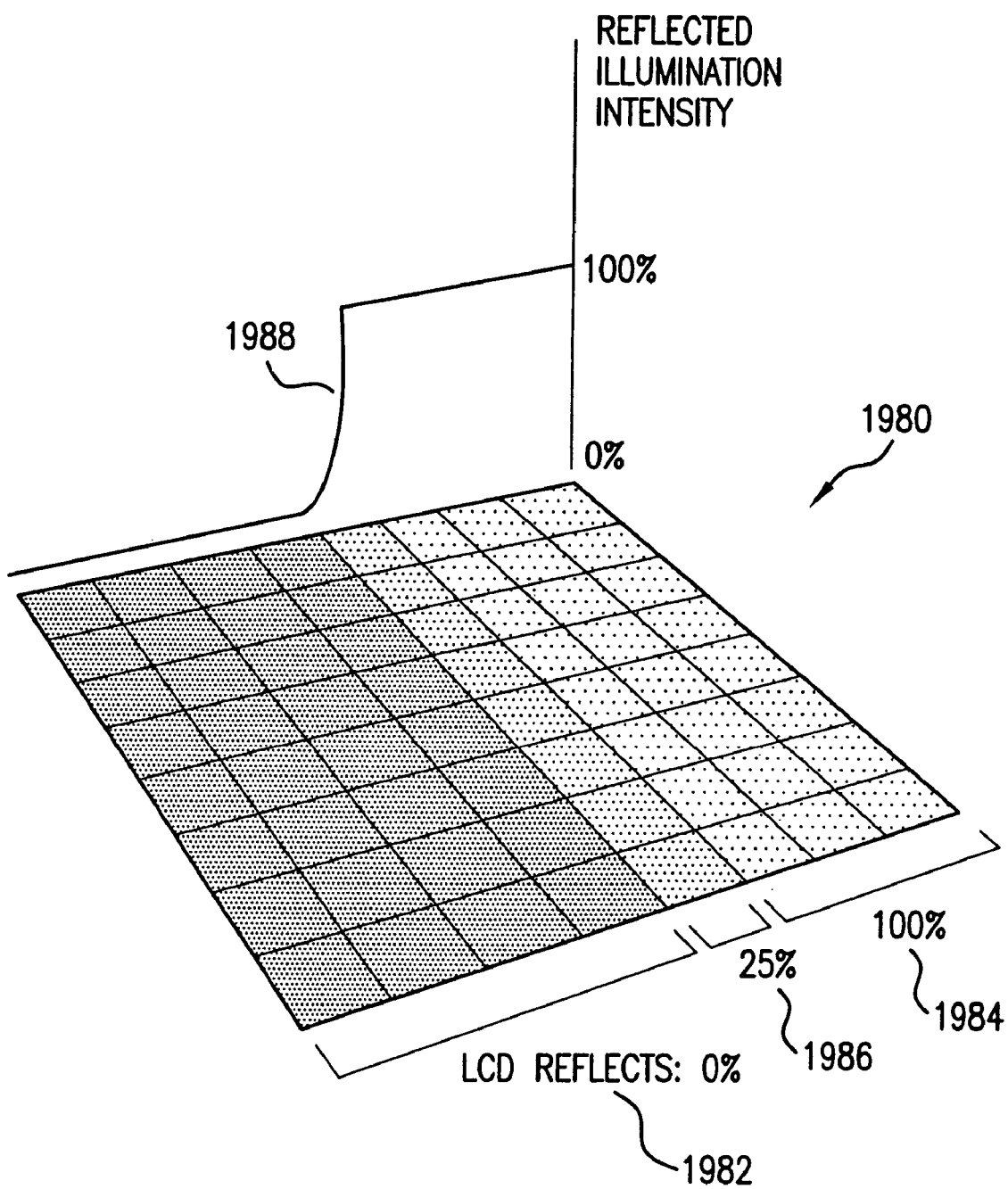

FIGS. 18 and 19 also illustrate the shifting of an exposed edge through the use of greyscaling as described in accordance with embodiments of the present invention. In FIG. 18, pixel rows 1882 of pixel grid 1880 are shown as completely "off." Pixel rows 1884 are shown as completely "on." Plot 1888 (shown above pixel grid 1880) shows a sharp transition between light and dark. FIG. 19 shows the movement of the exposed pattern edge. Pixel rows 1982 of pixel grid 1980 are shown as completely "off." Pixel rows 1984 are shown as completely "on." Pixel row 1986 is shown at an intermediate state of "on," in this case at 25% "on." Setting pixel row 1986 to an intermediate state of on, in effect, has moved the edge of the pattern slightly to the left. Plot 1988 (shown above pixel grid 1980) shows the transition between light and dark as a more graduated transition than that of FIG. 18.

CONCLUSION

This disclosure presents a maskless pattern writing system that acts as a light valve to control pattern imagery, on a pixel by pixel basis, for the purpose of direct writing patterns. While various embodiments of the present invention have been described above, it should be understood that they have been presented by way of example only, and not limitation. It will be understood by those skilled in the art that various changes in form and details can be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A method of generating a pattern for use in a maskless lithographic processing system using a pixel array of a liquid crystal programmable pattern generator having a plurality of pixels, comprising:
    generating an individual voltage level for respective pixels of a pixels array of a liquid crystal pattern generator; and
    applying the individual voltage level to the respective pixels of the pixel array to modulate a polarization state of a light beam interacting with the liquid crystal pattern generator so as to create a pattern image, wherein the individual voltage level corresponds to one of at least three different greyscale levels.

2. The method of claim 1, further comprising:
    receiving a control signal input from a controller based on pattern information provided to the controller, the control signal input defining the pattern image.

3. The method of claim 1, further comprising:
    polarizing the pattern image.

4. The method of claim 1, wherein the applying the individual voltage level comprises phase-shifting the pattern image by setting the individual voltage levels subsequent to one cycle of light.

5. The method of claim 1, wherein the applying the individual voltage level comprises shifting the pattern image by shifting settings of the individual voltage levels in one direction by the same number of pixel rows.

6. The method of claim 1, wherein the applying the individual voltage level comprises manipulating the edge of the pattern image by setting the individual voltage levels corresponding to individual pixels that are one of:
    part of an edge of the pattern image; and
    a pixel row beyond pixels that are part of the edge of the pattern image.

7. The method of claim 1, wherein the applying the individual voltage level to the respective pixels comprises applying one of:
    a maximum voltage;
    no voltage; and
    a percentage of the maximum voltage.

8. The method of claim 1, further comprising:
    reducing the pattern image with reduction optics for projection onto a substrate;
    positioning the substrate relative to the reduction optics; and
    projecting the pattern image onto the substrate.

9. The method of claim 8, wherein the reducing the pattern image comprises:

reflecting the light beam from the liquid crystal pattern generator through a polarizing beam splitter toward the reduction optics.

10. A maskless pattern generating system for use in a lithographic processing system, the maskless pattern system including a liquid crystal pixel array of a plurality of pixels and comprising:

means for generating an individual voltage level for respective pixels of a pixel array of the liquid crystal pattern generator; and means for applying the individual voltage level to the respective pixels of the pixel array to modulate a polarization state of a light beam interacting with the liquid crystal pattern generator so as to create a pattern image, wherein the individual voltage level corresponds to one of at least three different greyscale levels.

11. The maskless pattern generating system of claim 10, further comprising:

means for receiving a control signal input from a controller based on pattern information provided to the controller, the control signal input defining the pattern image.

12. The maskless pattern generating system of claim 10, further comprising:

means for polarizing the pattern image.

13. The maskless pattern generating system of claim 10, wherein the means for applying the individual voltage level is operable to phase shift the pattern image by setting the individual voltage levels subsequent to one cycle of light.

14. The maskless pattern generating system of claim 10, wherein the means for applying the individual voltage level is operable to shift the pattern image by shifting the settings of the individual voltage levels in one direction by the same number of pixel rows.

15. The maskless pattern generating system of claim 10, wherein the means for applying the individual voltage level is operable to manipulate an edge of the pattern image by setting the individual voltage levels corresponding to individual pixels that are one of:

part of the edge of the pattern image; and a pixel row beyond pixels that are part of the edge of the pattern image.

16. The maskless pattern generating system of claim 10, wherein the means for applying the individual voltage level to the respective pixels applies one of:

a maximum voltage;

no voltage; and a percentage of the maximum voltage.

17. The maskless lithography system of claim 10, further comprising:

means for reducing the pattern image for projection onto a substrate;

means for positioning the substrate relative to the means for reducing the pattern image; and means for projecting the pattern image onto the substrate.

18. A system for use in a lithographic processing system comprising:

a voltage generator configured to generate respective individual voltage levels; and a liquid crystal pattern generator comprising a pixel array of respective pixels;

wherein the respective individual voltage levels are applied to the respective pixels of the pixel array to modulate a polarization state of a light beam interacting with the liquid crystal pattern generator so as to create a pattern image, and wherein the respective individual voltage levels correspond to one of at least three different greyscale levels.

19. The system of claim 18, further comprising:

a controller configured to generate a control signal based on pattern information provided to the controller, the control signal defining the pattern image.

20. The system of claim 18, further comprising:

a polarizer configured to polarize the pattern image.

21. The system of claim 18, wherein the liquid pixel pattern generator is configured to phase-shift the pattern image by setting the respective individual voltage levels subsequent to one cycle of light.

22. The system of claim 18, wherein the liquid pixel pattern generator is configured to shift the pattern image based on shifting settings of the respective individual voltage levels in one direction by the same number of pixel rows.

23. The system of claim 18, wherein the liquid pixel pattern generator is configured to manipulate the edge of the pattern image based on setting the respective individual voltage levels corresponding to individual pixels that are one of:

part of an edge of the pattern image; and a pixel row beyond pixels that are part of the edge of the pattern image.

24. The system of claim 18, wherein the respective individual voltage levels comprise:

a maximum voltage;

no voltage; or a percentage of the maximum voltage.

\* \* \* \* \*

UNITED STATES PATENT AND TRADEMARK OFFICE
CERTIFICATE OF CORRECTION

PATENT NO. : 7,548,301 B2  Page 1 of 1
APPLICATION NO. : 11/337691
DATED : June 16, 2009
INVENTOR(S) : Harry Sewell It is certified that error appears in the above-identified patent and that said Letters Patent is hereby corrected as shown below:

In column 13, line 7, "maskless pattern system" should be --maskless pattern generating system--.

Signed and Sealed this

Twenty-fifth Day of August, 2009

David J. Kappos
*Director of the United States Patent and Trademark Office*